(12) United States Patent
Altmann et al.

(10) Patent No.: US 6,448,277 B2
(45) Date of Patent: Sep. 10, 2002

(54) VEGF RECEPTOR TYROSINE KINASE INHIBITORS

(75) Inventors: Karl-Heinz Altmann, Reinach (CH); Guido Bold, Gipf-Oberfrick (CH); Pascal Furet, Thann (FR); Paul William Manley, Arlesheim (CH); Jeanette Marjorie Wood, Biel-Benken (CH); Stefano Ferrari, Muttenz (CH); Francesco Hofmann, Bottmingen (CH); Jürgen Mestan, Denzlingen (DE); Andreas Huth, Berlin (DE); Martin Krüger, Berlin (DE); Dieter Seidelmann, Berlin (DE); Andreas Menrad, Oranienburg (DE); Martin Haberey, Berlin (DE); Karl-Heinz Thierauch, Berlin (DE)

(73) Assignees: Novartis AG, Basel (CH); Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/850,434

(22) Filed: May 7, 2001

Related U.S. Application Data

(63) Continuation of application No. PCT/EP99/08545, filed on Nov. 8, 1999.

(30) Foreign Application Priority Data

Nov. 10, 1998 (GB) .............................................. 9824579

(51) Int. Cl.[7] ...................... A61K 31/166; A61K 31/167; A61K 61/435; C07D 213/04

(52) U.S. Cl. ...................... 514/357; 514/359; 546/329; 546/339; 548/567

(58) Field of Search ................................ 546/152, 192, 546/290–329, 339; 548/400, 566, 567; 514/277, 357, 359

(56) References Cited

U.S. PATENT DOCUMENTS 3,226,394 A   12/1965   Schipper ..................... 260/295

FOREIGN PATENT DOCUMENTS

| EP | 0 947 500 A1 | 10/1999 |
|---|---|---|
| GB | 1189719 | 4/1970 |
| JP | 56-161362 | 12/1981 |
| JP | 9-59236 | 3/1997 |
| JP | 9059236 | * 3/1997 |
| JP | 10-259176 | 9/1998 |
| WO | 95/25723 | 9/1995 |
| WO | 96/09294 | 3/1996 |
| WO | 96/41795 | 12/1996 |
| WO | 98/17648 | 4/1998 |
| WO | 99/32477 | 7/1999 |
| WO | 99/54284 | 10/1999 |

OTHER PUBLICATIONS

Caplus, English Abstract JP9059236, Kawagoe Keiichi et al, Mar. 1997.*
Japan Tobacco Inc., Chemical Abstracts, 1982: 162351, (JP 56–161362, Dec. 11, 1981). (**).
Inaba et al., Chemical Abstracts 129:310895, Jun. 4, 1999, (JP 10–259176, Sep. 29, 1998).
Augustin, TiPS, vol. 19, "Antiangiogenic tumour therapy: will it work?" pp. 216–222, (Jun. 1998).
Hisano et al., Chem. Pharm.Bull., vol. 20, No. 12, "Syntheses and Pharmacological Activities of 2–Heterocyclic Substituted 4(3H)–Quinazolinone Derivatives," pp. 2575–2584, (1972).
Lüddens et al., European Journal of Pharmacology, vol. 344, "Structure—activity relationship of furosemide–derived compounds as antagonists of cerebellum–specific $GABA_A$ receptors," pp. 269–277, (1998).
Breier et al., Trends in Cell Biology, vol. 6, "The Role of Vascular Endothelial Growth Factor in Blood Vessel Formation," pp. 454–456, (Dec. 1996).
Mikhailitsyn et al., Chemical Abstracts, vol. 116, 41373f, p. 771, (1992) XP–002128306 (**).
Shani et al., Pharmacology, vol. 26, "Structure Activity Correlation for Diuretic Furosemide Congeners," pp. 172–180, (1983).

(List continued on next page.)

Primary Examiner—Alan L. Rotman
Assistant Examiner—Rita Desai
(74) Attorney, Agent, or Firm—George R. Dohmann

(57) ABSTRACT

Described are compounds of formula (I), wherein W is O or S; X is $NR_8$; Y is $CR_9R_{10}$—$(CH_2)n$ wherein $R_9$ and $R_{10}$ are independently of each other hydrogen or lower alkyl, and n is an integer of from and including 0 to and including 3; or Y is $SO_2$; $R_1$ is aryl; $R_2$ is a mono- or bicyclic heteroaryl group comprising one or more ring nitrogen atoms with the exception that $R_2$ cannot represent 2-phthalimidyl, and in case of $Y=SO_2$ cannot represent 2,1,3-benzothiadiazol-4-yl; any of $R_3$, $R_4$, $R_5$ and $R_6$, independently of the other, is H or a substituent other than hydrogen; and $R_7$ and $R_8$, independently of each other, are H or lower alkyl; or a N-oxide or a pharmaceutically acceptable salt thereof for the preparation of a pharmaceutical product for the treatment of a neoplastic disease which responds to an inhibition of the VEGF receptor tyrosine kinase activity. The compounds of formula (I) can be used for the treatment e.g. of a neoplastic disease, such as a tumor disease, of retinopathy and age-related macular degeneration.

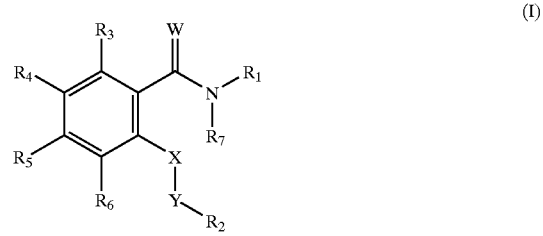

(I)

19 Claims, No Drawings

OTHER PUBLICATIONS

Tiwari et al., J.Chem.Soc.Pak, vol. 4, No. 2, "Visible Anti-fertility Compounds—Part IV: Syntheses of 2–(Phthalimido methylamino)–substituted benzanilides," pp. 115–117, (1982). (**).

Varnavas et al., Pharmazie, vol. 51, "Anthranoyl–anthranilic acid: a template for the development of a new class of cholecystokinin receptor ligands," pp. 697–700, (1996). (**).

* cited by examiner

VEGF RECEPTOR TYROSINE KINASE INHIBITORS

This application is a continuation of PCT Patent Application No. PCT/EP99/08545, filed Nov. 8, 1999, which in its entirety in herein by reference.

The invention relates to new benzamide derivatives, processes for the preparation thereof, the application thereof in a process for the treatment of the human or animal body, the use thereof—alone or in combination with one or more other pharmaceutically active compounds—for the treatment especially of a neoplastic disease, such as a tumor disease, of retinopathy and age-related macular degeneration; a method for the treatment of such a disease in animals, especially in humans, and the use of such a compound—alone or in combination with one or more other pharmaceutically active compounds—for manufacture of a pharmaceutical preparation (medicament) for the treatment of a neoplastic disease, of retinopathy and age-related macular degeneration.

Certain diseases are known to be associated with deregulated angiogenesis, for example diseases caused by ocular neovascularisation, such as retinopathies (including diabetic retinopathy), age-related macula degeneration, psoriasis, haemangioblastoma, haemangioma, arteriosclerosis, an inflammatory disease, such as a rheumatoid or rheumatic inflammatory disease, especially arthritis, such as rheumatoid arthritis, or other chronic inflammatory disorders, such as chronic asthma, arterial or post-transplantational atherosclerosis, endometriosis, and especially neoplastic diseases, for example so-called solid tumours and liquid tumours (such as leucemias).

According to recent findings, at the centre of the network regulating the growth and differentiation of the vascular system and its components, both during embryonic development and normal growth and in a wide number of pathological anomalies and diseases, lies the angiogenic factor known as "Vascular Endothelial Growth Factor" (=VGEF; originally termed "Vascular Permeability Factor",=VPF), along with its cellular receptors (see Breier, G., et al., Trends in Cell Biology 6, 454–6[1996] and references cited therein).

VEGF is a dimeric, disulfide-linked 46-kDa glycoprotein and is related to "Platelet-Derived Growth Factor" (PDGF). It is produced by normal cell lines and tumor cell lines, is an endothelial cell-specific mitogen, shows angiogenic activity in in vivo test systems (e.g. rabbit cornea), is chemotactic for endothelial cells and monocytes, and induces plasminogen activators in endothelial cells, which are then involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PLGF) and VEGF-C.

VEGF receptors are transmembranous receptor tyrosine kinases. They are characterized by an extracellular domain with seven immunoglobulin-like domains and an intracellular tyrosine kinase domain. Various types of VEGF receptor are known, e.g. VEGFR-1, VEGFR-2, and VEGFR-3.

A large number of human tumors, especially gliomas and carcinomas, express high levels of VEGF and its receptors. This has led to the hypothesis that the VEGF released by tumor cells could stimulate the growth of blood capillaries and the proliferation of tumor endothelium in a paracrine manner and thus, through the improved blood supply, accelerate tumor growth. Increased VEGF expression could explain the occurrence of cerebral oedema in patients with glioma. Direct evidence of the role of VEGF as a tumor angiogenesis factor in vivo has been obtained from studies in which VEGF expression or VEGF activity was inhibited. This was achieved with antibodies which inhibit VEGF activity, with dominant-negative VEGFR-2 mutants which inhibited signal transduction, or with the use of antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for those tumors which grow beyond a maximum diameter of about 1–2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between appptosis and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

Surprisingly, it has now been found that benzamide derivatives of formula I, described below, are a new class of compounds that have advantageous pharmacological properties and inhibit, for example, the activity of the VEGF receptor tyrosine kinase, the growth of tumors and VEGF-dependent cell proliferation, or the treatment of especially inflammatory rheumatic or rheumatoid diseases, such as rheumatoid arthritis, and/or pain, or the other diseases mentioned above and below.

The compounds of formula I open up, for example, an unexpected new therapeutic approach, especially for diseases in the treatment of which, and also for the prevention of which, an inhibition of angiogenesis and/or of the VEGF receptor tyrosine kinase shows beneficial effects.

FULL DESCRIPTION OF THE INVENTION

The invention relates the use of a compound of formula I

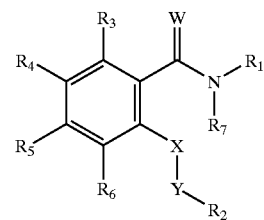

(I)

wherein
 W is O or S;
 X is $NR_8$;
 Y is $CR_9R_{10}$—$(CH_2)_n$ wherein
  $R_9$ and $R_{10}$ are independently of each other hydrogen or lower alkyl, and
  n is an integer of from and including 0 to and including 3; or
 Y is $SO_2$;
 $R_1$ is aryl;

R₂ is a mono- or bicyclic heteroaryl group comprising one or more ring nitrogen atoms with the exception that R₂ cannot represent 2-phthalimidyl, and in case of Y=SO₂ cannot represent 2,1,3-benzothiadiazol-4-yl;

any of $R_3$, $R_4$, $R_5$ and $R_6$, independently of the other, is H or a substituent other than hydrogen; and $R_7$ and $R_8$, independently of each other, are H or lower alkyl;

or a N-oxide or a pharmaceutically acceptable salt thereof for the preparation of a pharmaceutical product for the treatment of a neoplastic disease which responds to an inhibition of the VEGF receptor tyrosine kinase activity.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I wherein $R_9$ is lower alkyl) may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably,. lower alkyl is butyl, such as n-butyl, sec-butyl, isobutyl, tert-butyl, propyl, such as n-propyl or isopropyl, ethyl or preferably methyl.

The index n is preferably 0 or 1, especially 0.

Y is preferably methylene ($CH_2$) or ethylene ($CH_2$–$CH_2$), most preferably methylene.

"Aryl" is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, alkyl, substituted alkyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, lower alkenyl, lower alkanoyl, halogen-lower alkylmercapto, halogen-lower alkylsulfonyl, such as especially trifluoromethane sulfonyl, dihydroxybora (-B(OH)₂), heterocyclyl, and lower alkylene dioxy bound at adjacent C-atoms of the ring, such as methylene dioxy; aryl is preferably phenyl or naphthyl, which in each case is either unsubstituted or independently substituted by one or two substituents selected from the group comprising halogen, especially fluorine, chlorine, or bromine; hydroxy; hydroxy, etherified by lower alkyl, e.g. methyl, or by halogen-lower alkyl, e.g. trifluoromethyl; esterified carboxy, especially lower alkoxy carbonyl, e.g. methoxy carbonyl, npropoxy carbonyl or isopropoxy carbonyl; N-mono-substituted carbamoyl, in particular carbamoyl monosubstituted by lower alkyl, e.g. methyl, npropyl or isopropyl; lower alkyl, especially methyl, ethyl or propyl; substituted alkyl, especially lower alkyl, e.g. methyl or ethyl, substituted by lower alkoxy carbonyl, e.g. methoxy carbonyl or ethoxy carbonyl; halogen-lower alkyl, especially trifluoromethyl; lower alkylsulfinyl, such as methylsulfinyl, and lower alkanesulfonyl, such as methane sulfonyl. Aryl is preferably 3- or 4-chlorophenyl, 3-bromophenyl, 4-phenoxyphenyl, 2,3- or 4-methylphenyl, 4-methoxyphenyl, 3- or 4-tert-butylphenyl, 4-n-propylphenyl, 4-trifluoromethylphenyl, 3-trifluoromethylphenyl, 3-trifluoromethoxyphenyl, 3,4-(trifluoromethyl)phenyl, 3-fluoro-4-methylphenyl, 3-chloro-4-methylphenyl, 4-chloro-3-trifluoromethylphenyl, 3-chloro-5-trifluoromethylphenyl, 4-methylsulfinylphenyl, 4-methanesulfonylphenyl, 4-biphenyl, naphthyl, 2-naphthyl; tetrahydronaphthyl, in particular 5,6,7,8-tetrahydronaphthyl; hydroxynaphthyl, in particular 7-hydroxynaphthyl, 8-hydroxynaphthyl or 8-hydroxy-2-naphthyl; methoxynaphthyl, in particular 4-methoxy-2-naphthyl; halonaphthyl, in particular 4-chloronaphthyl or 3bromo-2-naphthyl.

Mono- or disubstituted amino is especially amino substituted by one or two radicals selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino.

Halogen is especially fluorine, chlorine, bromine, or iodine, especially fluorine, chlorine, or bromine.

In the preferred embodiment, alkyl has up to a maximum of 12 carbon atoms and is especially lower alkyl, especially methyl, or also ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Etherified hydroxy is especially $C_8$–$C_{20}$alkyloxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group $C_8$–$C_{20}$alkyloxy, such as n-decyloxy, halogen-lower alkoxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, isopropoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-mono- or N,N-disubstituted carbamoyl is especially substituted by one or two substituents independently selected from lower alkyl, phenyl-lower alkyl, and hydroxy-lower alkyl, at the terminal nitrogen atom.

Alkylphenylthio is especially lower alkylphenylthio.

Alkylphenylsulfonyl is especially lower alkylphenylsulfonyl.

Alkylphenylsulfinyl is especially lower alkylphenylsulfinyl.

Heterocyclyl is especially a five or six-membered heterocyclic system with 1 or 2 heteroatoms selected from the group comprising nitrogen, oxygen, and sulfur, which may be unsaturated or wholly or partly saturated, and is unsubstituted or substituted especially by lower alkyl, such as methyl; a radical selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylenedioxy, is preferably 3,4-methylenedioxyphenyl.

Heteroaryl refers to a heterocyclic moiety that is unsaturated in the ring binding the heteroaryl radical to the rest of the molecule in formula I and is preferably mono-, bi- or tricyclic, preferably mono- or bicyclic; where at least in the binding ring, but optionally also in any annealed ring, one or more, preferably 1 to 4, most preferably 3 or 4, carbon atoms are replaced each by a heteroatom selected from the group consisting of nitrogen, oxygen and sulfur; where the binding ring preferably has 5 to 12, more preferably 5 to 7 ring atoms; and may be unsubstituted or substituted by one or more, especially one or two, substitutents selected from the group defined above as substitutents for aryl, most preferably by lower alkyl, such as methyl; preferably heteroaryl is selected from thienyl, furyl, pyranyl, thianthrenyl, isobenzofuranyl, benzofuranyl, chromenyl, 2H-pyrrolyl, pyrrolyl, lower-alkyl substituted imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl; more preferably selected from the group consisting of triazolyl, especially 1,2,4-triazolyl, 1,2,3-triazolyl or 1,3,4-triazolyl, pyridyl, especially 2-, 3- or 4-pyridyl, indolyl, especially 3-indolyl, lower-alkylthiazolyl, especially 2-(4-methylthiazolyl), pyrrolyl, especially 1-pyrrolyl, lower alkylimidazolyl, especially 4-(1-methylimidazolyl), 4-(2-methylimidazolyl) or 4-(5-methylimidazolyl), benzimidazolyl, such as 1-benzimidazolyl, or tetrazolyl, such as 5-(1,2,3,4-tetrazolyl).

A mono- or bicyclic heteroaryl group comprising one or more ring nitrogen atoms is preferably a heteroaryl group as defined above for heteroaryl, with the proviso that preferably at least one nitrogen is present as ring heteroatom in the binding ring (that is, the ring from which the bond starts that binds the heteroaryl moiety to the rest of the molecule) and with the exception that $R_2$ cannot represent 2-phthalimidyl, and in case of $Y=SO_2R_2$ cannot represent 2,1,3-benzothiadiazol-4-yl. Preferred is imidazolyl, especially imidazol-4-yl, quinolyl, especially 3-, 4-, 5-quinolyl, naphthyridinyl, especially 3-(1,8-naphthyridinyl) or 4-(1,8-naphthyridinyl), or especially a moiety of the formula Ib or Ic

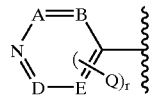

(Ib)

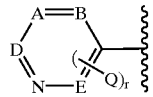

(Ic)

wherein r is 0 to 2,

A, B, D, and E are, independently of one another, N or CH, with the stipulation that not more than 2 of these radicals are N; preferably, each of A, B, D and E is CH; and Q is lower alkyl, especially methyl, hydroxy, lower alkoxy, especially methoxy, lower thioalkyl, especially methylthio, or halogen, especially fluoro, chloro or bromo.

Very preferably $R_2$ is 3-pyridyl, 4-pyridyl, 4-quinolinyl or 5-quinolinyl. Most preferably, $R_2$ is 4-pyridyl.

A substituent other than hydrogen is preferably selected from amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N- disubstituted carbamoyl, amidino, guanidino, mercapto, sulfo, lower alkylthio, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, lower alkenyl, lower alkanoyl, halogen-lower alkylmercapto, halogen-lower alkylsulfonyl, such as especially trifluoromethane sulfonyl and heterocyclyl. Two substitutents other than hydrogen bound at adjacent C-atoms of the ring can also represent lower alkylene dioxy, such as methylene dioxy ethylene dioxy. Preferably, a substituent other than hydrogen is lower alkyl or halogen, especially methyl, chloro or fluoro.

Preferably, $R_7$ and $R_8$ are hydrogen, and $R_3$, $R_4$, $R_5$ and $R_6$ each are independently hydrogen, chloro or fluorine.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, maleic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I and N-oxides thereof have valuable pharmacological properties, as described hereinbefore and hereinafter.

The efficacy of the compounds of the invention as inhibitors of VEGF-receptor tyrosine kinase activity can be demonstrated as follows:

Test for activity against VEGF-receptor tyrosine kinase. The test is conducted using Flt-1 VEGF-receptor tyrosine kinase. The detailed procedure is as follows: 30 $\mu$l kinase solution (10 ng of the kinase domain of Flt-1, Shibuya et al., Oncogene 5, 519–24 [1990]) in 20 mM Tris.HCl pH 7.5, 3 mM manganese dichloride ($MnCl_2$), 3 mM magnesium chloride ($MgCl_2$), 10 $\mu$M sodium vanadate, 0.25 mg/ml polyethylenglycol (PEG) 20000, 1 mM dithiothreitol and 3 $\mu$g/$\mu$l poly(Glu,Tyr) 4:1 (Sigma, Buchs, Switzerland), 8 $\mu$M [$^{33}$P]-ATP (0.2 $\mu$Ci), 1% dimethyl sulfoxide, and 0 to 100 $\mu$M of the compound to be tested are incubated together for 10 minutes at room temperature. The reaction is then terminated by the addition of 10 $\mu$l 0.25 M ethylenediaminetetraacetate (EDTA) pH 7. Using a multichannel dispenser (LAB SYSTEMS, USA), an aliquot of 20 $\mu$l is applied to a PVDF (=polyvinyl difluoride) Immobilon P membrane (Millipore, USA), through a Millipore microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 $\mu$l Microscint® ($\beta$-scintillation counter liquid). $IC_{50}$-values are determined by linear regression analysis of the percentages for the inhibition of each compound in three concentrations (as a rule 0.01, 0.1, and 1 $\mu$mol). The $IC_{50}$-values that can be found with compounds of formula I are in the range of 0.01 to 100 $\mu$M, preferably in the range from 0.01 to 50 $\mu$M.

The antitumor efficacy of the compounds of the invention can be demonstrated in vivo as follows:

In vivo activity in the nude mouse xenotransplant model:female BALB/c nude mice (8–12 weeks old), Novartis Animal Farm, Sisseln, Switzerland) are kept under sterile conditions with water and feed ad libitum. Tumors are induced either by subcutaneous injection of tumor cells into mice (for example, Du 145 prostate carcinoma cell line (ATCC No. HTB 81; see Cancer Research 37, 4049–58 (1978)) or by implanting tumor fragments (about 25 mg) subcutaneously into the left flank of mice using a 13-gauge trocar needle under Forene® anaesthesia (Abbott, Switzerland). Treatment with the test compound is started as soon as the tumor has reached a mean volume of 100 mm$^3$. Tumor growth is measured two to three times a week and 24 hours after the last treatment by determining the length of two perpendicular axes. The tumor volumes are calculated in accordance with published methods (see Evans et al., Brit. J. Cancer 45, 466–8 [1982]). The antitumor efficacy is determined as the mean increase in tumor volume of the treated animals divided by the mean increase in tumor volume of the untreated animals (controls) and, after multiplication by 100, is expressed as T/C%. Tumor regression (given in %) is reported as the smallest mean tumor volume in relation to the mean tumor volume at the start of treatment. The test compound is administered daily by gavage.

As an alternative other cell lines may also be used in the same manner, for example:

the MCF-7 breast adenocarcinoma cell line (ATCC No. HTB 22; see also J. Natl. Cancer Inst. (Bethesda) 51, 1409–16 [1973]);

the MDA-MB 468 breast adenocarcinoma cell line (ATCC No. HTB 132; see also in Vitro 14, 911–15 [1978]);

the MDA-MB 231 breast adenocarcinoma cell line (ATCC No. HTB 26; see also J. Natl. Cancer Inst. (Bethesda) 53, 661–74 [1974]);

the Colo 205 colon carcinoma cell line (ATCC No. CCL 222; see also Cancer Res. 38. 1345–55 [1978]);

the HCT 116 colon carcinoma cell line (ATCC No. CCL 247; see also Cancer Res. 41. 1751–6 [1981]);

the DU145 prostate carcinoma cell line DU 145 (ATCC No. HTB 81; see also Cancer Res. 37, 4049–58 [1978]); and the PC-3 prostate carcinoma cell line PC-3 (ATCC No. CRL 1435; see also Cancer Res. 40, 524–34 [1980]).

The inhibition of VEGF-induced KDR-receptor autophosphorylation can be confirmed with a further in vitro experiment in cells: transfected CHO cells, which permanently express human VEGF receptor (KDR), are seeded in complete culture medium (with 10% fetal call serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours' incubation at 37° C., recombinant VEGF is added; the final VEGF concentration is 20 ng/ml). After a further five minutes' incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −200° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an antiphosphotyrosine antibody coupled with alkaline phosphatase (PY20:AP from Transduction Laboratories). The (plates are washed again and the) binding of the antiphosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition). Compounds of formula I here preferably show ED50 values in the range of 0.001 μM to 6 μM, preferably 0.005 to 0.5 μM.

A compound of formula I or a N-oxide thereof inhibits to varying degrees also other tyrosine kinases involved in signal transduction which are mediated by trophic factors, for example Abl kinase, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase (see House et al., Europ. J. Biochem. 140, 363–7[1984]). The erbB2 kinase can be isolated, and its activity determined, using methods known per se (see T. Akiyama et al., Science 232, 1644 [(1986]).

On the basis of these studies, a compound of formula I according to the invention shows therapeutic efficacy especially against disorders dependent on protein kinase, especially proliferative diseases.

The usefulness of a compound of the formula I in the treatment of arthritis as an example of an inflammatory rheumatic or rheumatoid disease can be demonstrated as follows:

The well-known rat adjuvant arthritis model (Pearson, Proc. Soc. Exp. Biol. 91, 95–101 (1956)) is used to test the anti-arthritic activity of compounds of the formula I or salts thereof. Adjuvant Arthritis can be treated using two different dosing schedules: either (i) starting time of immunisation with adjuvant (prophylactic dosing); or from day 15 when the arthritic response is already established (therapeutic dosing). Preferably a therapeutic dosing schedule is used. For comparison, a cyclooxygenase-2 inhibitor, such as 5-bromo-2-(4-fluorophenyl)-3-[4-(methylsulfonyl)phenyl]thiophene or diclofenac, is administered in a separate group.

In detail, male Wistar rats (5 animals per group, weighing epproximately 200 g, supplied by Iffa Credo, France) are injected i.d. (intra-dermally) at the base of the tail with 0.1 ml of mineral oil containing 0.6 mg of lyophilised heat-killed *Mycobacterium tuberculosis*. The rats are treated with the test compound (3, 10 or 30 mg/kg p.o. once per day), or vehicle (water) from day 15 to day 22 (therapeutic dosing schedule). At the end of the experiment, the swelling of the tarsal joints is measured by means of a mico-calliper. Percentage inhibition of paw swelling is calculated by reference to vehicle treated arthritic animals (0% inhibition) and vehicle treated normal animals (100% inhibition).

The activity of compounds of the formula I against pain can be shown in the following model of nociception (pain). In this model, the hyperalgesia caused by an intra-planar yeast injection is measured by applying increased pressure to the foot until the animal vocalizes or withdraws its foot from the applied pressure pad. The model is sensitive to COX inhibitors, and diclofenac at 3 mg/kg is used as a positive control.

Method: The baseline pressure required to induce vocalization or withdrawal of the paw of male Sprague Dawley rats (weighing approximately 180 g, supplied by Iffa Credo, France) is measured (2 hours before treatment), followed by an intra-planar injection of 100 μl of a 20% yeast suspension in water in the hind paw. The rats are treated orally with the test compound (3, 10 or 30 mg/kg), diclofenac (3 mg/kg) or vehicle (saline) p.o. 2 hours later (time point 0 hours), and the pressure test is repeated 1 and 2 hours after dosing. Using the standard apparatus supplied by Ugo Basile, Italy, the pressure required to induce vocalisation or paw withdrawal of the compound-treated rats at these time points is compared to that of vehicle-treated animals.

On the basis of these studies, a compound of formula I surprisingly is appropriate for the treatment of inflammatory (especially rheumatic or rheumatoid) diseases and/or pain. The compounds of the formula I especially IA, (or an N-oxide thereof) according to the invention also show therapeutic efficacy especially against other disorders dependent on protein kinase, especially proliferative diseases.

On the basis of their efficacy as inhibitors of VEGF-receptor tyrosine kinase activity, the compounds of the formula I primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomenmlonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, endometriosis, chronic asthma, arterial or post-transplantational atherosclerosis, neurodegenerative disorders and especially neoplastic diseases (solid tumours, but also leucemias and other "liquid tumours", especially those expressing c-kit, KDR or flt-1), such as especially breast cancer, cancer of the colon, lung cancer (especially small-cell lung cancer), cancer of the prostate or Kaposi's sarcoma. A compound of formula I (or an N-oxide thereof) inhibits the growth of tumours and is especially suited to preventing the metastatic spread of tumours and the growth of micrometastases.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more cytostatic or cytotoxic compounds, for example a chemotherapeutic agent or several selected from the group comprising an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula I or a N-oxide thereof for the inhibition of VEGF-receptor tyrosine activity, either in vitro or in vivo.

A compound of formula I or a N-oxide thereof may also be used for diagnostic purposes, for example with tumors that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

With the groups of preferred compounds of formula I and N-oxides thereof mentioned hereinafter, definitions of substituents from the general definitions mentioned hereinbefore may reasonably be used, for example, to replace more general definitions with more specific definitions or especially with definitions characterized as being preferred;

Furthermore, the invention relates to the use of a compound of formula I wherein the radicals and symbols have the meanings as defined above, or a N-oxide or a pharmaceutically acceptable salt thereof for the preparation of a pharmaceutical product for the treatment of retinopathy or age-related macula degeneration.

Furthermore, the invention relates to a method for the treatment of a neoplastic disease which responds to an inhibition of the VEGF-receptor tyrosine kinase activity, which comprises administering a compound of formula I or a N-oxide or a pharmaceutically acceptable salt thereof, wherein the radicals and symbols have the meanings as defined above, in a quantity effective against the said disease, to a warm-blooded animal requiring such treatment.

Furthermore, the invention relates to a method for the treatment of retinopathy or age-related macular degeneration, which comprises administering a compound of formula I or a N-oxide or a pharmaceutically acceptable salt thereof, wherein the radicals and symbols have the meanings as defined above; in a quantity effective against said diseases, to a warm-blooded animal requiring such treatment.

The invention relates in particular to a compound of formula I wherein

W is O or S;

X is $NR_8$;

Y is $CR_9R_{10}$—$(CH_2)_n$ wherein
  $R_9$ and $R_{10}$ are independently of each other hydrogen or lower alkyl, and
  n is an integer of from and including 0 to and including 3; or Y is $SO_2$;

$R_1$ is aryl;

$R_2$ is a mono- or bicyclic heteroaryl group comprising one or more ring nitrogen atoms with the exception that $R_2$ cannot represent 2-phthalimidyl, and in case of Y=$SO_2$ cannot represent 2,1,3-benzothiadiazol-4-yl;

any of $R_3$, $R_4$, $R_5$ and $R_6$, independently of the other, is H or a substituent other than hydrogen; and $R_7$ and $R_8$, independently of each other, are H or lower alkyl;

with the exception of the compound of formula I wherein W is O, X is $NR_8$, Y is $CH_2$, $R_1$ is 4-chlorophenyl, $R_2$ is 2-pyridyl, $R_3$, $R_4$, $R_5$, $R_7$ and $R_8$ are each H and $R_6$ is chloro;

or a N-oxide or a pharmaceutically acceptable salt thereof.

Preferred are compounds of formula I wherein

W is O or S;

X is $NR_8$;

Y is $CHR_9$—$(CH_2)_n$ wherein
  $R_9$ is hydrogen or lower alkyl, and
  n is an integer of from and including 0 to and including 3; or Y is $SO_2$;

$R_1$ is aryl;

$R_2$ is a mono- or bicyclic heteroaryl group comprising one or more ring nitrogen atoms with the exception that $R_2$ cannot represent 2-phthalimidyl, and in case of Y=$SO_2$ cannot represent 2,1,3-benzothiadiazol4-yl;

any of $R_3$, $R_4$, $R_5$ and $R_6$, independently of the other, is H or a substituent other than hydrogen; and $R_7$ and $R_8$, independently of each other, are H or lower alkyl;

with the exception of the compound of formula I wherein W is O, X is $NR_8$, Y is $CH_2$, $R_1$ is 4-chlorophenyl, $R_2$ is 2-pyridyl, $R_3$, $R_4$, $R_5$, $R_7$ and $R_8$ are each H and $R_6$ is chloro;

or a salt thereof.

In particular, preferred compounds of formula I are those in which

W is O or S;

X is $NR_8$;

Y is $CHR_9$—$(CH_2)_n$ wherein
$R_9$ is H or lower alkyl, and
n is 0 to 3; or

Y is $SO_2$;

$R_1$ is phenyl that is unsubsituted or substituted by up to three substituents selected from amino, mono- or disubstituted amino wherein the substituents are selected independently from lower alkyl, hydroxy-lower alkyl, phenyl-lower alkyl, lower alkanoyl, benzoyl and substituted benzoyl wherein the phenyl radical is substituted by one or two substituents selected from nitro, amino, halogen, N-lower alkylamino, N,N-di-lower alkylamino, hydroxy, cyano, carboxy, lower-alkoxycarbonyl, lower alkanoyl and carbamoyl, and phenyl-lower alkoxycarbonyl wherein the phenyl radical radical is substituted by one or two substituents selected from nitro, amino, halogen, N-lower alkylamino, N,N-di-lower alkylamino, hydroxy, cyano, carboxy, lower-alkoxycarbonyl, lower alkanoyl and carbamoyl; lower alkyl; substituted lower alkyl where up to three substituents are present independently selected from the group containing halogen, N-lower alkylamino, N,N-di-lower alkylamino, N-lower alkanoylamino, hydroxy, cyano, carboxy, lower alkoxycarbonyl and phenyl-lower alkoxycarbonyl; hydroxy, lower alkoxy; phenyl-lower alkoxy; phenyloxy;

halogen-lower alkoxy, lower alkanoyloxy; benzoyloxy; lower alkoxycarbonyloxy; phenyl-lower alkoxycarbonyloxy; nitro; cyano; carboxy; lower alkoxycarbonyl; phenyl-lower alkoxycarbonyl; phenyloxycarbonyl; lower alkylcarbonyl; carbamoyl; N-mono- or N,N-disubstituted carbamoyl that is substituted by one or two substituents independently selected from lower alkyl, phenyl-lower alkyl and hydroxy-lower alkyl, at the terminal nitrogen atom; amidino; guanidino; mercapto; sulfo; lower alkylthio; phenylthio; phenyl-lower alkylthio; lower alkylphenylthio; lower alkylsulfinyl; phenylsulfinyl; phenyl-lower alkylsulfinyl; lower alkylphenylsulfinyl; lower alkanesulfonyl; phenylsulfonyl; phenyl-lower alkylsulfonyl; lower alkylphenylsulfonyl; lower alkenyl; lower alkanoyl; halogen-lower alkylmercapto; halogen-lower alkylsulfonyl; dihydroxybora (—$B(OH)_2$); and lower alkylene dioxy bound at adjacent C-atoms of the ring;

$R_2$ is imidazolyl, quinolyl, naphthyridinyl, or a moiety of the formula Ib or Ic

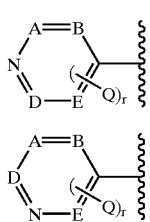

(Ib)

(Ic)

wherein r is 0 to 2;

A, B, D, and E are, independently of one another, N or CH, with the stipulation that not more than 2 of these radicals are N; preferably; and Q is lower alkyl, hydroxy, lower alkoxy, lower thioalkyl or halogen;

any of $R_3$, $R_4$, $R_5$, and $R_6$, independently of the other, is H, fluorine or lower alkyl; and $R_7$ and $R_8$, independently of each other, are H or lower alkyl;

or a N-oxide or a pharmaceutically acceptable salt thereof.

More specifically, preference is given to a compound of formula I wherein

W is O;

X is $NR_8$;

Y is $CHR_9$—$(CH_2)_n$ wherein
$R_9$ is H or methyl, and
n is 0;

or Y is $SO_2$;

$R_1$ is phenyl, naphthyl or 5,6,7,8-tetrahydronaphthyl which is in each case either unsubstituted or independently substituted by one or two substituents selected from the group comprising halogen; lower alkyl; lower alkoxy; hydroxy; phenyl; phenoxy; halogen-lower alkoxy, halogen-lower alkyl; lower alkoxycarbonyl; N-lower alkyl carbamoyl; lower alkylsuffinyl; lower alkanesulfonyl; and lower alkoxycarbonyl lower alkyl;

$R_2$ is imidazolyl, quinolyl, naphthyridinyl, 2-methyl-pyridin-4-yl, 3-pyridyl or 4-pyridyl;

any of $R_3$, $R_4$, $R_5$ and $R_6$, independently of the other, are H, methyl or chloro; or $R_3$ and $R_4$ together represent methylene dioxy and $R_5$ and $R_6$, independently of the other, are H, methyl or chloro; and $R_7$ and $R_8$, independently of each other, are H, fluorine or methyl;

or a N-oxide or a pharmaceutically acceptable salt thereof.

Even more specifically, preference is given to a compound of formula I wherein

W is O;

X is $NR_8$

Y is $CHR_9$—$(CH_2)$, wherein
$R_9$ is H or methyl, and
n is 0;

or Y is $SO_2$;

$R_1$ is phenyl which is either unsubstituted or independently substituted by one or two substituents selected from the group comprising halogen; lower alkyl; halogen-lower alkyl; lower alkylsulfinyl; and lower alkanesulfonyl;

$R_2$ is imidazolyl, quinolyl, naphthyridinyl, 2-methyl-pyridin-4-yl, 3-pyridyl or 4-pyridyl;

any of $R_3$, $R_4$, $R_5$ and $R_6$, independently of the other, is H or methyl; and $R_7$ and $R_8$, independently of each other, are H or methyl;

or a N-oxide or a pharmaceutically acceptable salt thereof.

Mostly preferred are compounds of formula I wherein

W is O;

X is $N_8$

Y is $CHR_9$—$(CH_2)_n$ wherein
$R_9$ is H or methyl, and
n is 0;

or Y is $SO_2$;

$R_1$ is phenyl which is either unsubstituted or independently substituted by one or two substituents selected from the group comprising halogen; lower alkyl; halogen-lower alkyl; lower alkylsulfinyl; and lower alkanesulfonyl;

R₂ is imidazolyl, quinolyl, 2-methyl-pyridin-4-yl or 4-pyridyl;

any of R₃, R₄, R₅ and R₆, independently of the other, is H or methyl; and

R₇ and R₈, independently of each other, are H or methyl; or a salt thereof.

Especially preferred are compounds of formula I wherein

W is O;

X is NR₈;

Y is CH₂;

R₁ is phenyl, naphthyl or 5,6,7,8-tetrahydronaphthyl which is in each case either unsubstituted or independently substituted by one or two substituents selected from the group comprising halogen; lower alkyl; lower alkoxy; hydroxy; phenyl; phenoxy; halogen-lower alkoxy; lower alkoxycarbonyl; N-lower alkyl carbamoyl; and lower alkoxycarbonyl lower alkyl;

R₂ is 4-pyridyl;

any of R₃, R₄, R₅ and R₆, independently of the other, are H, methyl or chloro; or R₃ and R₄ together represent methylene dioxy and R₅ and R₆, independently of the other, are H, methyl or chloro; and R₇ and R₈ are H;

or a N-oxide or a pharmaceutically acceptable salt thereof.

More special preference is given to a compound of formula I such as is mentioned in the Examples below, or a pharmaceutically acceptable salt thereof, especially a compound of the formula I or a salt thereof specifically mentioned in the Examples.

High preference is given to a compound selected from

2-[(4-pyridyl)methyl]amino-N-(4-trifluoromethylphenyl)benzamide;
2-[(4-pyridyl)methyl]amino-N-(4-chlorophenyl)benzamide;
2-[(4-pyridyl)methyl]amino-N-(4-methylphenyl)benzamide;
2-[(4-pyridyl)methyl]amino-N-(3-fluoro-4-methylphenyl)benzamide;
2-[(4-pyridyl)methyl]amino-N-(4-chloro-3-trifluoromethylphenyl)benzamide;
2-[(4-pyridyl)methyl]amino-N-(3-chloro-6-trifluoromethylphenyl)benzamide;
2-[(4-pyridyl)methyl]amino-N-(4-methylphenyl)-6-methylbenzamide; and
2-[(4-quinolyl)methyl]amino-N-(4-chlorophenyl)benzamide;

or a pharmaceutically acceptable salt thereof.

Furthermore, high preference is given to a compound selected from

2-[(4-pyridyl)methyl]amino-N-[3-fluoro-(4-trifluoromethyl)phenyl]benzamide;
2-[(4-pyridyl)methyl]amino-N-phenylbenzamide;
2-[(4-pyridyl)methyl]amino-N-[4-fluoro-3-(trifluoromethyl)phenyl]benzamide;
2-[(4-pyridyl)methyl]amino-N-[3-fluoro-5-(trifluoromethyl)phenyl]benzamide;
2-[(4-pyridyl)methyl]amino-N-[3,5-(bistrifluoromethyl)phenyl]benzamide;
2-[(4-pyridyl)methyl]amino-N-[3,4-bis-(trifluoromethyl)phenyl]benzamide;
2-[(4-pyridyl)methyl]amino-N-[3-methoxy-5-(trifluoromethyl)phenyl]benzamide;
2-[(4-pyridyl)methyl]amino-N-[3-(trifluoromethyl)phenyl]benzamide;
2-[(4-pyridyl)methyl]amino-N-[3-(1,1-dimethylethyl)phenyl]benzamide;
2-[(4-pyridyl)methyl]amino-N-(3-cyanophenyl)benzamide;
2-[(4-pyridyl)methyl]amino-N-[(3-methylthio)phenyl]benzamide;
2-[(4-pyridyl)methyl]amino-N-(3-acetylaminophenyl)benzamide;
2-[(4-pyridyl)methyl]amino-N-[3-[(aminocarbonyl)amino]phenyl]benzamide;
2-[(4-pyridyl)methyl]amino-N-[3-(dimethylamino)pheny)]benzamide;
5-methoxy-2-[(4-pyridyl)methyl]amino-N-[3-(trifluoromethyl)phenyl]benzamide;
3-methyl-2-[(4-pyridyl)methyl]amino-N-[3-(trifluoromethyl)phenyl]benzamide;
4,5-difluoro-2-[(4-pyridyl)methyl]amino-N-[3-(trifluoromethyl)phenyl]benzamide;
2-[(4-pyridyl)methyl]amino-N'-methyl-N'-[3-(trifluoromethyl)phenyl]benzamide;
2-[(4-pyridyl)methyl]amino-N-[(3-methylsulphonyl)phenyl]benzamide;
2-[(4-pyridyl)methyl]amino-N-[(3-methylsulphonyl)phenyl]benzamide;
2-[(4-pyridyl)methyl]amino-N-[4-(1,1-dimethylethyl)phenyl]benzamide;
2-[(4-pyridyl)methyl]amino-N-(3-chlorophenyl)benzamide;
2-[(4-pyridyl)methyl]amino-N-(3-bromophenyl)benzamide;
2-[(4-pyridyl)methyl]amino-N-(3-methylphenyl)benzamide;
2-[(4-pyridyl)methyl]amino-N-(3-benzoylphenyl)benzamide;
2-[(4-pyridyl)methyl]amino-N-[3-(aminocarbonyl)phenyl]benzamide;
2-[(3-pyridyl)methyl]amino-N-[3-(trifluoromethyl)pheny]benzamide;
2-[(4-quinolinyl)methyl]amino-N-[3-(trifluoromethyl)pheny]benzamide;
2-[(5-quinolinyl)methyl]amino-N-[3-(trifluoromethyl)pheny]benzamide;
2-[(4-(2-methyl)pyridyl)methyl]amino-N-[3-(trifluoromethyl)phenyl]benzamide;
2-[(4-(1,2-dihydro-2-oxo)pyridyl)methyl]amino-N-[3-(trifluoromethyl)phenyl]benzamide;
2-[(4-quinolinyl)methyl]amino-N-(4-chlorophenyl)benzamide;
2-[(2-imidazolyl)methyl]amino-N-(4-chlorophenyl)benzamide;
2-[2-(4-pyridyl)ethyl]amino-N-[3-(trifluoromethyl)phenyl]benzamide;
2-[2-(3pyridyl)ethyl]amino-N-[3-(trifluoromethyl)phenyl]benzamide;
2-[1-methyl-2-(3-pyridyl)ethyl]amino-N-[3-(trifluoromethyl)phenyl]benzamide;
2-[(1-oxido-4-pyridyl)methyl]amino-N-[3-(trifuoromethyl)pheny]benzamide; and
2-[(4-pyridyl)methyl]methylamino-N-[3-(trifluoromethyl)phenyl]benzamide;
2-[(4-pyridyl)methyl]amino-N-(4-chloronaphthyl)benzamide;
6-methyl-2-[(4-pyridyl)methyl]amino-N-(4-chlorophenyl)benzamide;
6-chloro-2-[(4-pyridyl)methyl]amino-N-(4-chlorophenyl)benzamide;
3,4-methylendioxy-6-[(4-pyridyl)methyl]amino-N-(4-chlorophenyl)benzamide;
4,5-dimethyl-2-[(4-pyridyl)methyl]amino-N-(4-chlorophenyl)benzamide;

5-chloro-2-[(4-pyridyl)methyl]amino-N-(4-n-propylphenyl) benzamide;
2-[(4-pyridyl)methyl]amino-(4-n-propylphenyl)benzamide;
2-[(4-pyridyl)methyl]amino-N-(7-hydroxynaphthyl) benzamide;
2-[(4-pyridyl)methyl]amino-N-(8-hydroxy-2-naphthyl) benzamide;
4-chloro-2-[(4-pyridyl)methyl]amino-N-(4-chlorophenyl) benzamide;
5-methyl-2-[(4-pyridyl)methyl]amino-N-(4-chlorophenyl) benzamide;
2-[(4-pyridyl)methyl]amino-N-(5,6,7,8-tetrahydronaphthyl) benzamide;
2-[(4-pyridyl)methyl]amino-N-(4-biphenyl)benzamide;
5-chloro-2-[(4-pyridyl)methyl]amino-N-(4-chlorophenyl) benzamide;
2-[(4-pyridyl)methyl]amino-N-(naphthyl)benzamide;
2-[(4-pyridyl)methyl]amino-N-(2-napthyl)benzamide;
2-[(4-pyridyl)methyl]amino-N-(4-methoxyphenyl) benzamide;
2-[(4-pyridyl)methyl]amino-N-(trifuoromethoxy)phenyl] benzamide;
2-[(4-pyridyl)methyl]amino-N-(4-methoxy-2-naphthyl) benzamide;
2-[(4-pyridyl)methyl]amino-N-(3-bromo-2-naphthyl) benzamide;
2-[(4-pyridyl)methyl]amino-N-[4-(isopropoxycarbonyl) phenyl]benzamide;
2-[(4-pyridyl)methyl]amino-N-[4-(trifuoromethoxy)phenyl] benzamide;
2-[(4-pyridyl)methyl]amino-N-[4-(isopropylcarbamoyl) phenyl]benzamide;
2-[(4-pyridyl)methyl]amino-N-(3-chloro-4-methylphenyl) benzamide;
2-[(4-pyridyl)methyl]amino-N-(2-methylphenyl) benzamide;
2-[(4-pyridyl)methyl]amino-N-[3-(methoxycarbonylmethyl)phenyl]benzamide;
2-[(4-pyridyl)methyl]amino-N-(4-phenoxyphenyl) benzamide;

or a pharmaceutically acceptable salt thereof.

A compound of the invention may be prepared by processes that, though not applied hitherto for the new compounds of the present invention, are known per se, especially a process characterized in that a) for the synthesis of a compound of the formula I wherein X represents $NR_8$, where $R_8$ is hydrogen and Y represents $CHR_9$—$(CH_2)_n$, each as indicated for a compound of formula I and the remaining symbols $R_1$, $R_2$, $R_3$, $R_4$, $R_5$ and $R_6$ are as defined for a compound of the formula I an aniline derivative of the formula II.

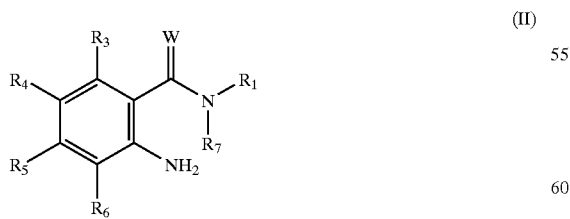

wherein W, $R_1$, $R_3$, $R_4$, $R_5$, $R_6$ and $R_7$ are as defined for a compound of the formula I is reacted with a carbonyl compound of the formula III

wherein n, $R_2$ and $R_9$ are as defined for a compound of the formula I in the presence of a reducing agent; or b) for the synthesis of a compound of the formula I wherein Y is $SO_2$ and the remaining symbols $R_1$, $R_2$, $R_3$, $R_4$, $R_5$, $R_6$, $R_7$, W and X are as defined for a compound of the formula I an aniline derivative of the formula II as defined under process variante a) is reacted with an acid of the formula IVa

 (IVa)

or a reactive derivative thereof; or with a compound of formula IVb,

 (IVb)

wherein Hal' is chloro, bromo or iodo; or c) for the synthesis of compounds of the formula I wherein X represents $NR_8$, Y represents $CR_9R_{10}$—$(CH_2)_n$ and the remaining symbols $R_1$, $R_2$, $R_3$, $R_4$, $R_5$, $R_6$, $R_7$ and $R_8$ are as defined for a compound of the formula I a halogen derivative of the formula V.

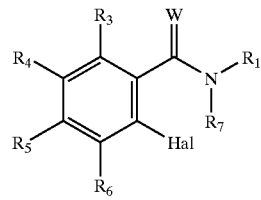 (V)

wherein Hal represents iodine, bromine or chlorine and W, $R_1$, $R_3$, $R_4$, $R_5$, $R_6$ and $R_7$ are as defined for a compound of the formula I is reacted with an amine of the formula VI

 (VI)

wherein n, $R_2$, $R_8$, $R_9$ and $R_{10}$ are as defined for a compound of the formula I in the presence of an appropriate catalyst such as a palladium catalyst, for example as generated in situ from tris (dibenzylideneacetone)-dipalladium [O] and 2,2'-bis(diphenylphosphino)-1,1-binaphthyl in an inert solvent such as toluene, in the presence of an aprotic base such as sodium t-butoxide or caesium carbonate, or a nickel catalyst, such as dibromobis (bipyridyl)-nickel[2] in a solvent such as isopropylmethyl ketone, or a copper catalyst, such as copper(I)iodide in a solvent such as dimethylformamide;

d) for the synthesis of compounds of the formula I wherein X represents $NR_8$, Y represents $CH_2$, W is O, $R_2$ is 4-pyridyl, $R_7$ and $R_8$ are each H and and $R_1$, $R_3$, $R_4$, $R_5$ and $R_6$ are as defined for a compound of the formula I a compound of formula VII

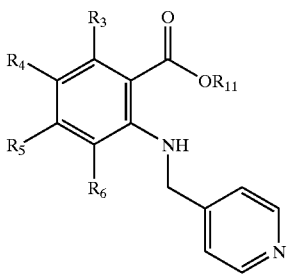

(VII)

wherein $R_3$, $R_4$, $R_5$ and $R_6$ are as defined for a compound of the formula I and $R_{11}$ is lower alkyl, is reacted with a compound of formula VIII $$H_2NR_1 \quad (VIII)$$

wherein $R_1$ is as defined for a compound of formula I in the presence of trimethylaluminium in an inert solvent, e.g. toluol;

where the starting compounds defined in a), b), c) or d) may also be present with functional groups in protected form if necessary and/or in the form of salts, provided a salt-forming group is present and the reaction in salt form is possible;

any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

Detailed Description of the Process Variants

In the more detailed description of the process below, $R_1$, $R_2$, $R_3$, $R_4$, $R_5$, $R_6$, $R_7$, $R_8$, $R_9$, $R_{10}$, X, Y and W are as defined for compounds of formula 1 unless otherwise indicated.

Process a) (Reductive Alkylation)

The carbonyl compound of the formula III may also be present in the form of reactive derivative; however, the free aldehyde or ketone is preferred.

Reactive derivatives of the compounds of formula III are, for example, corresponding bi-sulfite adducts or especially semiacetals, acetals, semiketals or ketals of compounds of formula III with alcohols, for example lower alkanols; or thioacetals or thioketals of compounds of formula III with mercaptans, for example lower alkanesulfides.

The reductive alkylation is preferably carried out with hydrogenation in the presence of a catalyst, especially a noble metal catalyst, such as platinum or especially palladium, which is preferably bonded to a carrier material, such as carbon, or a heavy metal catalyst, such as Raney nickel, at normal pressure or at pressures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkanecarboxylic acids, especially acetic acid, or a sulfonic acid, such as p-toluenesulfonic acid; in customary solvents, for example alcohols, such as methanol or ethanol, or ethers, for example cyclic ethers, such as tetrahydrofuran, in the presence or absence of water.

Process b) (Condensation)

In this process the reagents introducing the radical $R_2Y$- contain either a free sulfo group (formula IVa) or are in the form of a reactive derivative thereof, for example in the form of a derived activated ester or reactive anhydride, or in the form of a reactive cyclic amide, or contain the sulfo group in the form of a sulfonic acid halide (formula IVb). Reactive derivatives may also be formed in situ.

In formula IVb Hal' is preferably chlorine or bromine. The reaction is carried out in a suitable solvent, e.g. dichloromethane, e.g. at room temperature or the reflux temperature of the solvent, in the presence of a suitable amine, e.g. N-ethyldiisopropylamine, and optionally 4-dimethylaminopyridine.

The amino group of compounds of formula II that participates in the reaction preferably is in free form, especially when the sulfonyl group reacting therewith is present in reactive form; it may, however, itself have been derivatised, for example by reaction with a phosphite, such as diethylchlorophosphite, 1,2-phenylene chlorophosphite, ethyldichlorophosphite, ethylene chlorophosphite or tetraethylpyrophosphite. A derivative of such a compound having an amino group is, for example, also a carbamic acid halide or an isocyanate, the amino group that participates in the reaction being substituted by halocarbonyl, for example chlorocarbonyl, or modified in the form of an isocyanate group, respectively.

The condensation of activated esters, reactive anhydrides or reactive cyclic amides with the corresponding amines is customarily carried out in the presence of an anorganic base, such as an alkaline metal hydrogencarbonate of carbonate, or especially an organic base, for example simple tri-lower alkylamines, for example triethylamine or tributylamine, or one of the above-mentioned organic bases. If desired, a condensation agent is additionally used, for example as described for free carboxylic acids.

The condensation is preferably carried out in an inert, aprotic, preferably anhydrous, solvent or solvent mixture, for example in a carboxylic acid amide, for example formamide or di-methylformamide, a halogenated hydrocarbon, for example methylene chloride, carbon tetrachloride or chlorobenzene, a ketone, for example acetone, a cyclic ether, for example tetetrahydrofuran or dioxane, an ester, for example ethyl acetate, or a nitrile, for example acetonitrile, or in a mixture thereof, as appropriate at reduced or elevated temperature, for example in a temperature range of from approximately −40° to approximately +100° C., preferably from approximately −10° to approximately +70°C., and when arylsulfonyl esters are used also at approximately from +1000 to +200° C., especially at temperatures of from 10° to 30° C., and if necessary under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone may also be added where appropriate.

Process c) (Amination)

The amination process is preferably carried out as an Ullmann type reaction using a copper catalyst, such as copper[O] or a coppery[I] compound such as copper[I] oxide, copper[I]-bromide or copper[I]iodide in the presence of a suitable base (such as a metal carbonate, for example potassium carbonate) to neutralise the acid generated in the reaction. This reaction is reviewed in Houben-Weyl "Methoden der Organischen Chemie", Band 11/1, page 32–33.

1958, in Organic Reactions, Volume 14, page 19–24, 1965 and by J. Lindley (1984) in Tetrahedron, Volume 40, page 1433–1456. The amount of catalyst is typically in the range of 1 to 20 mole percent. The reaction is carried out in an inert, aprotic solvent such as an ether (for example dimethoxyethane or dioxan) or an amide (for example dimethylformamide or N-methylpyrrolidone), under an inert atmosphere in the temperature range of 60–180° C.

An alternative amination process involves using a Group VIII element, where the metal core of the catalyst should be a zero-valent transition metal, such as palladium or nickel, which has the ability to undergo oxidative addition to the Aryl-Halogen bond. The zero valent state of the metal may be generated in situ from the M[II] state. The catalyst complexes may include chelating ligands, such as alkyl, aryl or heteroaryl derivatives of phoshines or biphosphines, imines or arsines. Preferred cataysts contain palladium or nickel. Examples of such catalysts include palladium[II] chloride, palladium[II]acetate, tetrakis(triphenylphosphine) palladium[O] and nickel[II]acetylacetonate. The metal catayst is typically in the range of 0.1 to 10 mole percent. The chelating ligands may be either monodentate, as in the case for example of trialkyphosphines, such as tributylphosphine, triaryl phosphines, such as tri-(orth-tolyl)phosphine, and triheteroaryl phosphines, such as tri-2-furyl-phosphine; or they may be bidentate such as in the case of 2,2'-bis9diphenylphosphino)-1,1'binaphthyl, 1,2-bis(diphenylphosphino)ethane, 1,1'-bis(diphenylphosphino)ferrocene and 1-(N,N-dimethyl-amino)-1'-(dicyclohexylphosphino)biphenyl. The supporting ligand may be added may be complexed to the metal centre in the form of a metal complex prior to being added to the reaction mixture or may be added to the reaction mixture as a separate compound. The supporting ligand is typically present in the range 0.01 to 20 mole percent It is often necessary to add a suitable base to the reaction mixture, such as a trialkylamine (for example diisoprpylethylamine or 1,5-diazabicyclo[5,4,0]undec-5-ene), a Group I alkali metal alkoxide (for example potassium tertiary-butoxide) or carbonate (for example caesium carbonate) or potassium phosphate. The reaction is typically carried out in an inert aprotic solvent such as an ether (for example dimethoxyethane or dioxan) or an amide (for example dimethylformamide or N-methylpyrrolidone), under an inert atmosphere in the temperature range of 60–80° C.

The amination is preferably carried out in an inert, aprotic, preferably anhydrous, solvent or solvent mixture, for example in a carboxylic acid amide, for example dimethylformamide or dimethylacetamide, a cyclic ether, for example tetrahydrofuran or dioxane, or a nitrile, for example acetonitrile, or in a mixture thereof, at an appropriate temperature, for example in a temperature range of from approximately 400 to approximately 180° C., and if necessary under an inert gas atmosphere, for example a nitrogen or argon atmosphere.

Process d) (Amidation)

In this process first a dimethylaluminium amide is prepared in situ from $Me_3Al$ and an appropriate amine. Then the esters to be treated are added and the reaction is carried out at a temperature between 20° C. and 150° C., preferably between 100° C. and 120° C., e.g. at 110° C., depending on the reactivity of the amide and the ester, in an inert solvent like benzene, toluene, xylene, tetrahydrofuran, $C_6$–$C_{10}$ alkanes, or a mixture thereof.

N-Oxides can be obtained in a known matter by reacting a compound of formula I with hydrogen peroxide or a peracid, e.g. 3-chloroperoxy-benzoic acid, in an inert solvent, e.g. dichloromethane, at a temperature between –10° C. and +35° C., e.g. 0° C. or room temperature.

Protecting Groups

If one or more other functional groups, for example carboxy, hydroxy, amino, or mercapto, are or need to be protected in a compound of formulae II, III and/or IV, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesise", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosauren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistiy of carbohydrates: monosaccharides and derivatives*), Georg Thieme Verlag, Stuttgart 1974.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

A compound of formula I wherein W is O, can be converted into the respective compound wherein W is S, for example, by using an appropriate sulfur compound, e.g. using reaction with Lawesson's reagent (2,4-bis-(4-methoxyphenyl)2,4-dithioxo-1,2,3,4-dithiophosphate) in a halogenated carbon hydrate, such as dichloromethane, or an aprotic solvent, such as toluene or xylene, at temperatures from about 30° C. to reflux.

A compound of the formula I wherein any one or both of $R_7$ and $R_9$ is hydrogen and is part of a sulfonamide (Y is $SO_2$) bond can be converted to the respective compound wherein $R_7$ and/or $R_9$ is lower alkyl by reaction e.g. with a diazo lower alkyl compound, especially diazomethane, in an inert solvent, preferably in the presence of a noble metal catalyst, especially in dispersed form, e.g. copper, or a noble metal salt, e.g. cupper(I)-chloride or copper(II)-sulfate. Also reaction with lower alkylhalogenides is possible, or with other leaving group carrying lower alkanes, e.g. lower alkyl alcohols esterified by a strong organic sulfonic acid, such as a lower alkane sulfonic acid (optionally substituted by halogen, such as fluoro), an aromatic sulfonic acid, for example unsubstituted or substituted benzene-sulfonic acid, the substituents preferably being selected from lower alkyl, such as methyl, halogen, such as bromo, and/or nitro, e.g. esterified by methane sulfonic acid, trimethane sulfonic acid or p-toluol sulfonic acid.

Also, in a compound of the formula I wherein $R_8$ is hydrogen and Y is $CR_9R_{10}(CH_2)_n$, the alkylation may be made with such alkylating agents.

In both cases, the alkylation takes place especially in aqueous solution and/or in the presence of polar solvents, typically alcohols, for example methanol, ethanol, isopropanol, or ethylene glycol, ethers, typically dioxane, amides, typically dimethylformamide, or phenols, typically phenol, and also under non-aqueous conditions, in non-polar solvents, typically benzene and toluene, or in benzene/water emulsions, where applicable in the presence of acidic or basic catalysts, for example leaches, typically sodium hydroxide solution, or in the presence of solid-phase catalysts, typically aluminium oxide, that have been doped with hydrazine, in ethers, for example diethylether, generally at temperatures from about 0° C. to the boiling temperature of the corresponding reaction mixture, preferably between 200° C. and reflux temperature, if necessary under increased pressure, e.g. in a sealed tube, a temperature in excess of boiling point also being possible, and/or under inert gas, typically nitrogen or argon.

It should be emphasized that reactions analogous to the conversions mentioned in this chapter may also take place at the level of appropriate intermediates.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from $-100°$ C. to about 190° C., preferably from about $-80°$ C. to about 150° C., for example at $-80°$ to $-60°$ C., at room temperature, at $-20$ to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers. or enantiomers, or into any mixtures of isomers, e.g. racemates or diastereomeric mixtures, typically as described under "Additional process steps".

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitriles, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to or in analogy to the processes and process steps defined in the Examples.

The compounds of formula I including their salts, are also obtainable in the form of hydrates, or their crystals can include for example the solvent used for crystallization (present as solvates).

Pharmaceutical Preparations, Methods, and Uses

The present invention relates also to pharmaceutical compositions that comprise a compound of formula I or a N-oxide thereof as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of formula I or N-oxides thereof for the preparation of pharmaceutical preparations which comprise compounds of formula I or N-oxides thereof as active component (active ingredient).

In the preferred embodiment, a pharmaceutical preparation is suitable for administration to a warm-blooded animal, especially humans or commercially useful mammals suffering from a disease responsive to an inhibition of angiogenesis or of VEGF-receptor tyrosine kinase, for example psoriasis or especially a neoplastic disease, and. comprises an effective quantity of a compound of formula I or N-oxides thereof for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against the said diseases a novel compound of formula I or N-oxides thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active Ingredient Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® [polyoxyethylene(20)sorbitan mono-oleate; trademark of ICI Americas, Inc, USA].

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid 6sters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester; Gattefossé, France), and/or "Miglyol 812" (triglyceride of saturated fatty acids of chain length $C_8$ to $C_{12}$ from Hüls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethyl cellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially a disease which responds to an inhibition of the VEGF-receptor tyrosine kinase or an inhibition of angiogenesis, especially a corresponding neoplastic disease or also psoriasis. The compounds of formula I or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I or a pharmaceutically acceptable salt thereof, especially a compound of formula I or N-oxides thereof which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, especially a neoplastic disease or also psoriasis, more especially if the disease responds to an inhibition of angiogenesis or an inhibition of VEGF-receptor tyrosine kinase.

The present invention relates especially also to the use of a compound of formula I or N-oxides thereof, or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of VEGF-receptor tyrosine kinase or an inhibition of angiogenesis, especially a neoplastic disease or also psoriasis, more especially if the said disease responds to an inhibition of VEGF-receptor tyrosine kinase or angiogenesis.

The present invention relates especially also to the use of a compound of formula I or N-oxides thereof, or a pharmaceutically acceptable salt thereof, especially a compound of formula I which is said to be preferred, or a pharmaceutically acceptable salt thereof, for the preparation of a pharmaceutical formulation for the therapeutic and also prophylactic management of one or more of the diseases mentioned hereinabove, especially a neoplastic disease or also psoriasis, more especially if the disease responds to an inhibition of VEGF-receptor tyrosine kinase or angiogenesis.

The preferred dose quantity, composition, and preparation of pharmaceutical formulations (medicines) which are to be used in each case are described above.

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the formula II, III, IVa, IVb, V, VI, VII and VIII are known, are commercially available, or can be synthesized in analogy to or according to methods that are known in the art.

For example, an aniline of the formula II can be prepared from a nitro compound of the formula IX,

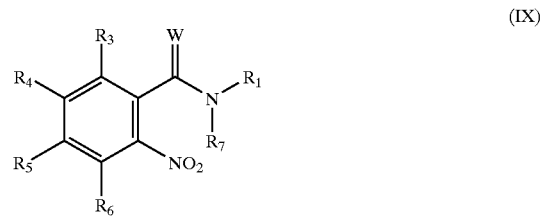

(IX)

wherein $R_1$, $R_3$ to $R_7$ and W have the meanings as given under formula I.

The reduction preferably takes place in the presence of a suitable reducing agent, such as tin(II) chloride or hydrogen in the presence of an appropriate catalyst, such as Raney nickel (then preferably the hydrogen is used under pressure, e.g. between 2 and 20 bar) or $PtO_2$, in an appropriate solvent, e.g. an alcohol, such as methanol. The reaction temperature is preferably between 0 and 80° C., especially 15° to 30° C.

A nitro compound of the formula IX is accessible by reaction of an acid of the formula X,

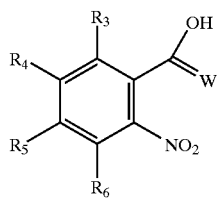
(X)

wherein W is oxygen and R₃ to R₆ are as defined above, or an activated derivative thereof, is reacted with an amine of the formula XI,

(XI)

wherein R₁ and R₇ are as defined under formula I e.g. in the presence of a coupling agent, such as dicyclohexylcarbodiimide, at a temperature between 0° C. and 50° C., preferably at room temperature.

If required, W=O can be changed to W=S with Lawesson's agent, as described above for the analogous conversion of a compound of formula I with W=O into one with W=S.

It would also be possible to first reduce the nitro compound of the formula X to the corresponding aniline compound under reaction conditions analogous to those for the reduction of nitro compounds of the formula IX and then react the resulting anilino compound with the amino compound of formula XI under analogous conditions as decribed above. However, it may then be nesessary to protect the aniline amino group.

An anthranilic acid derivative of the formula VII is accesible through the reductive amination reaction of a compound of formula XI

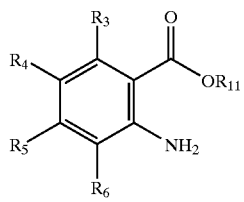
(XII)

wherein R₃, R₄, R₅ and R₆ are as defined for a compound of the formula I and R₁ is lower alkyl or aryl, by first reacting the compound of formula XII with 4-pyridine-carbaldehyde and then with a reducing agent, e.g. sodium cyanotrihydrido-borate, in a one-step procedure in a lower alkanol, e.g. methanol, ethanol or propanol, at a temperature between 0° C. and 50° C., e.g. at room temperature.

The reaction sequence of first obtaining an imine starting from the amine of formula XII and then reducing it can also be accomplished in separate reaction steps. Reagents which can be used to add hydrogen to an imine double bond include borane in tetrahydrofuran, LiAlH₄, NaBH₄, sodium in ethanol and hydrogen in the presence of a catalyst.

All remaining starting materials of are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described under "protecting groups" or in the Examples.

EXAMPLES

The following Examples serve to illustrate the invention without limiting the invention in its scope.

Temperatures are measured in degrees celsius (CC). Unless otherwise indicated, the reactions take place at room temperature.

Preparation of Intermediates

1. Intermediate 1a: 2-Nitro-N-(4-trifluoromethylphenyl)benzamide

A solution containing 2-nitrobenzoyl chloride (Fluka, Buchs, Switzerland) (1.97 mL, 15 mmol) and 4-dimethylaminopyridine (Fluka, Buchs, Switzerland) (10 mg) in dichloromethane (10 mL) is added to a stirred mixture of 4-aminobenzotrifluoride (Ruka, Buchs, Switzerland) (2.66 g, 16.5 mmol) and triethylamine (1.90 g, 18.8 mmol) in dichloromethane (100 mL) under an argon atmosphere and the mixture is stirred for 16 hours at 25° C. The stirred mixture is then treated with a saturated aqueous solution of sodium hydrogen carbonate (50 mL) and then extracted with dichoromethane (2×50 mL). The combined extracts are dried (Na₂SO₄), filtered and the solvent is evaporated off under reduced pressure to yield the crude product which is purified by column chromatography on silica gel, eluent 10–50% ethyl acetate in hexane, to give the title compound as a colourless crystalline solid.

Intermediate 1b: 2-Nitro-N-[3-fluoro-(4-trifluoromethyl)phenyl]benzamide

A solution of 4-amino-2-fluorobenzotrifluoride (fluorochem, Derbyshire, England; 14.4 g, 75 mmol) in ethyl acetate (150 mL) was added to a stirred solution of sodium hydroxide (3.30 g, 82.5 mmol) in water, at room temperature. This stirred solution was then treated dropwise over 30 minutes with a solution of 2-nitrobenzoyl chloride (11.0 mL, 82.5 mmol in dry ethyl acetate (110 mL). The resulting mixture was then stirred overnight at ambient temperature. The mixture is then extracted with ethyl acetate (3×100 mL). The combined extracts are sequentially washed with water (2–100 mL), hydrochloric aciid (2–100 mL of 2M), water (2–100 mL), saturated aqueous sodium hydrogen carbonate solution (2–100 mL) and saturated aqueous sodium chloride (1–100 mL), dried (Na₂SO₄), filtered and the solvent is evaporated off under reduced pressure to yield the crude product which is purified by recrystallisation from ethyl acetate-hexane to give the title compound as a colourless crystalline solid, m.p. 185–189° C.

The following compounds are prepared analogously by utilising the appropriate amine (the supplier of which is e.g. Fluka or Aldrich, both Buchs, Switzerland, or mentioned in parenthesis):

(1c) 2-Nitro-N-(4-chlorophenyl)benzamide, utilizing 4-chloroaniline (1d) 2-Nitro-N-(4-methylphenyl)benzamide, utilizing 4-methylaniline (1e) 2-Nitro-N-(3-fluoro-4-methylphenyl) benzamide, utilizing 3-fluoro-4-methylaniline (Riedelde Haen, Seelze, Germany)

(1f) 2-Nitro-N-[4-chloro-(3-trifluoromethyl)phenyl] benzamide, utilizing 4-chloro-3-(trifluoromethyl) benzenamine (1g) 2-Nitro-N-[3-chloro-(5-trifluoromethyl)phenyl] benzamide, utilizing 3-amino-5-chloro-benzotrifluoride, prepared from 4-amino-3-chloro-5-nitrobenzotrifluoride (Maybridge Chemical Co. Ltd.) as described in European Patent Application EP 0 516 297)

(1h) 2-Nitro-N-[4-fluoro-(3-trifluoromethyl)phenyl] benzamide, utilizing 4-fluoro-3-(trifluoromethyl) benzenamine (1i) 2-Nitro-N-[3-fluoro-(5-trifluoromethyl)phenyl] benzamide, utilizing 3-fluoro-5-trifluoromethyl) benzenamine (Fluorochem, Derbyshire, England)

(1j) 2-Nitro-N-[3,5-(bis-trifluoromethyl)phenyl] benzamide, utilizing 3,5-(bistrifluoromethyl)-benzenamine (1k) 2-Nitro-N-[3,4-(bis-trifluoromethyl)phenyl] benzamide, utilizing 3,4-(bistrifluoromethyl)-benzenamine (1k) 2-Nitro-N-[3-methoxy-(5-trifluoromethyl) phenyl]benzamide, utilizing 3-methoxy-5-(trifluoromethyl)benzenamine (1m) 2-Nitro-N-[3-(trifluoromethyl)phenyl] benzamide, utilizing 3-(trifluoromethyl) benzenamine (1n) 2-Nitro-N-[3-(1,1-dimethyl)ethyl)phenyl] benzamide, utilizing 3-tert-butylaniline (1o) 2-Nitro-N-(3-cyanophenyl)benzamide, utilizing 3-cyanobenzenamine (1p) 2-Nitro-N-[(3-methylthiophenyl)benzamide, utilizing 3-methylthiobenzenamine (1q) 2-Nitro-N-[3-[(1-oxoethyl)amino]phenyl] benzamide, utilizing 3-methylthiobenzenamine (Pfaltz and Bauer Inc, Connecticut, USA)

(1r) 2-Nitro-N-[3-1(aminocarbonyl)amino]phenyl] benzamide, utilising 3-aminophenylurea (Bayer Organica, Leverkusen, Germany)

(1s) 2-Nitro-N-[3-(dimethylamino)phenyl)] benzamide, uilising N,N-dimethyl-1,3-benzenediamine, dihydrochloride (Lancaster Synthesis, Lancashire, England)

(1t) 5-Methoxy-2-nitro-N-[3-(trifluoromethyl) pheny]benzamide, utilising 5-methoxy-2-nitrobenzoyl chloride (which may be prepared as described by Sami Khan and LaMontagne, J. Med. Chem. 1979;22:1005–1008, from 5-methoxy-2-nitrobenzoic acid) and 3-(trifluoromethyl) benzenamine (1u) 3-Methyl-2-nitro-N-[3-(trifluoromethyl)phenyl] benzamide, utilising 3-methyl-2-nitrobenzoyl chloride (which may be prepared as described by Edge et al, J. Chem. Soc. Perkin Trans. 1 1982; 1701–1714, from 3-methyl-2-nitrobenzoic acid) and 3-(trifluoromethyl)benzenamine (1v) 4,5-Difluoro-2-nitro-N-[3-(trifluoromethyl) phenyl]benzamide, utilising 4,5-diluoro-2-nitrobenzoyl chloride prepared from 4,5-difluoro-2-nitrobenzoic acid as described in German Patent Application DE 3717904

(1w) 2-Nitro-N-methyl-N-[3-(trifluoromethyl) phenyl]benzamide, utilizing N-methyl-3-(trifluoromethyl)benzenamine prepared as described by Berbalk et al, Monatshefte Chemie 1976;107: 401–404, from 3-(trifluoromethyl)benzenamine (1x) 2-Bromo-N-[3-(trifluoromethyl)phenyl] benzamide, utilising 2-bromobenzoyl chloride in lieu of 2-nitrobenzoyl chloride and 3-(trifluoromethyl)benzenamine Intermediate 1y: 2-Nitro-N-[(3-methylsulphonyl) phenyl]benzamide 3-Chloroperoxybenzoic acid (71.8 g of 55%, 229 mmol) is added to a stirred mixture of 2-Nitro-N-(3-methylthiophenyl)benzamide (Intermediate 1p; 22.0 g, 76.3 mmol) in dichloromethane (1 L) at 0° C. The resulting mixture is then stirred at 35° C. for 70 hours. The mixture is then washed sequentially with aqueous sodium hydroxide (2–100 mL) and aqueous sodium thiosulphate (2–50 mL of 10%). The organic phase is dried ($Na_2SO_4$), filtered and the solvent is evaporated off under reduced pressure to yield the crude product which is purified by column chromatography on silica gel, eluent 50% ethyl acetate in hexane and recrystallised from diisopropyl ether to give the title compound as a colourless crystalline solid, m.p. 172–173° C.

2. Intermediate 2a: 2-Amino-N-(4-trifluoromethylphenyl)benzamide

A solution of intermediate 1a (1.92 g, 6.19 mmol) in methanol (200 mL) is hydrogenated at 5 bar over Raney nickel (400 mg) at 21° C. The calculated amount of hydrogen is taken up in 1 hour. The mixture is then filtered and the solvent is evaporated off under reduced pressure to yield the crude product which is purified by recrystallisation from dichloromethane-hexane to give the title compound as a colourless crystalline solid, m.p. 160–161° C.

The following compounds are prepared analogously by utilising the appropriate amine:

(2b) 2-Amino-N-[3-fluoro-4-(trifluoromethyl) phenyl]benzamide, m.p. 135–137° C., utilising intermediate 1b (2c) 2-Amino-N-(4-chlorophenyl)benzamide, m.p. of the hydrochloride salt 156–173° C., utilising intermediate 1c (2d) 2-Amino-N-(4-methylphenyl)benzamide, utilising intermediate 1d.

(2e) 2-Amino-N-(3-fluoro-4-methylphenyl) benzamide, m.p. 149–151° C., utilising intermediate 1e (2f) 2-Amino-N-[4-chloro-3-(trifluoromethyl) phenyl]benzamide, m.p. 148–150° C., utilising intermediate 1f (2g) 2-Amino-N-[3-chloro-5-(trifluoromethyl) phenyl]benzamide, m.p. 174–175° C., utilising intermediate 1g (2h) 2-Amino-N-[4-fluoro-3-(trifluoromethyl) phenyl]benzamide, m.p. 159–162° C., utilising intermediate 1h (2i) 2-Amino-N-[3-fluoro-5-(trifluoromethyl) phenyl]benzamide, m.p. 142–144° C., utilising intermediate 1i (2j) 2-Amino-N-[3,5-(bis-trifluoromethyl)phenyl) benzamide, m.p. 192–193° C., utilising intermediate 1j (2k) 2-Amino-N-[3,4-(bis-trifluoromethyl)phenyl] benzamide, utilising intermediate 1k.

(2l) 2-Amino-N-[3-methoxy-5-(trifluoromethyl) phenyl]benzamide, m.p. 125–126° C., utilising intermediate 1l (2m) 2-Amino-N-3-(trifluoromethyl)phenyl] benzamide, m.p. 131–133° C., utilising intermediate 1m (2n) 2-Amino-N-[3-(1,1-dimethyl)ethyl)phenyl] benzamide, m.p. 84–86° C., utilising intermediate 1n (2o) 2-Amino-N-(3-cyanophenyl)benzamide, m.p. 161–163° C., utilising intermediate 1o (2p) 2-Amino-N-(3-methylthiophenyl)benzamide, m.p. 88–90° C., utilising intermediate 1p (2q) 2-Amino-N-[3[(1-oxoethyl)amino]phenyl] benzamide, m.p. 132–134° C., utilising intermediate 1q (2r) 2-Amino-N-[3-[(aminocarbonyl)amino]phenyl] benzamide, m.p. 187–189° C., utilising intermediate 1r (2s) 2-Amino-N-[3-(dimethylamino)phenyl] benzamide, m.p. 109–110° C., utilising intermediate 1s (2t) 2-Amino-5-methoxy-N-[3-(trifluoromethyl) phenyl]benzamide, m.p. 98–99° C., utilising intermediate 1t (2u) 2-Amino-N-[3-methyl-N-[3-(trifluoromethyl) phenyl]benzamide, m.p. 103–108° C., utilising intermediate 1u (2v) 2-Amino-N-[4,5-difluoro-N-[3-(trifluoromethyl)phenyl]benzamide, m.p. 198–200° C., utilising intermediate 1v (2w) 2-Amino-N'-[-methyl-N'-[3-(trifluoromethyl) phenyl]benzamide, m.p. 61–64° C., utilising intermediate 1w Intermediate 2x: 2-Amino-N-[(3-methylsulphonyl) phenyl]benzamide A solution of intermediate 1y (22.0 g, 68.7 mmol in methanol (1500 mL) is hydrogenated at 7 bar over 10% palladium on carbon (1.0 g) at 22° C. The calculated amount of hydrogen is taken up in 1 hour. The mixture is then filtered and the solvent is evaporated off under reduced pressure to yield the crude product which is purified by column chromatography on silica gel, eluent ethyl acetate and recrystallisation from diisopropyl ether-hexane to give the title compound as a colourless crystalline solid, m.p. 190–193° C.

Intermediate 2y: 2-Amino-N-[(3-methylsulphinyl) phenyl)benzamide

A solution of intermediate 2p (2.58 g, 10 mmol) in ethanol (100 mL) is added dropwise over 30 min to a stirred solution of sodium metaperiodate (2.25 g, 10.5 mmol) mixed solvent (100 ml of ethanol and 100 ml of $H_2O$) at 0° C. The mixture is stirred at 5° C. for 17 hours and then diluted with water (600 mL) and extracted with dichloromethane (3×150 mL). The combined extracts are dried ($Na_2SO_4$), filtered and the solvent is evaporated off under reduced pressure to yield the crude product which is purified by column chromatography on silica gel, eluent ethyl acetate and recrystallised from isopropanol-diisopropylether to give the title compound as a colourless crystalline solid, m.p. 117–121° C.

Intermediate 2z: 2-Amino N-[4-(1,1-dimethyl)ethyl) phenyl]benzamide

A solution of 4-tert-butylaniline (9.00 g, 60.3 mmol) in dimethylformamide (20 mL) is added to a stirred solution of isatoic anhydride (9.75 g, 60 mmol) in dimethylformamide (80 mL) at 100° C. The mixture is stirred at 100° C. for 4 hours. The solvent is then evaporated off under reduced pressure to give a residue which is dissolved in ethyl acetate (300 mL) and washed with saturated aqueous ammonium chloride solution. The solution is dried ($Na_2SO_4$), filtered and the solvent is evaporated off under reduced pressure to yield the product which is purified by column chromatography on silica gel, eluent 10% ethyl acetate in hexane and recrystallised from t butylmethyl ether-cyclohexane to give the title compound as a colourless crystalline solid, m.p. 132–134° C.

The following compounds are prepared analogously by utilising the appropriate amine:

(2aa) 2-Amino-N-(3-chlorophenyl)benzamide, m.p. 136–137° C., utilizing 3-chloroaniline (2ab) 2-Amino-N-(3-bromophenyl)benzamide, m.p. 150–153° C., utilizing 3-bromoaniline (2ac) 2-Amino-N-(3-methylphenyl)benzamide, m.p. 115–117° C., utilizing 3-methylaniline (2ad) 2-Amino-N-(3-benzoylphenyl)benzamide, as a yellow oil, utilizing (3-aminophenyl) phenylmethanone (2ae) 2-Amino-N-[(3-aminocarbonyl)phenyl] benzamide, utilizing 3-aminobenzamide Intermediate 2af: 2-Amino-(4-methylphenyl)-6-methylbenzamide (i) 2-{[1,1-Dimethylethoxy)carbonyl]amino}-6-methylbenzoic acid A stirred solution of 2-amino-6-methylbenzoic acid (9.90 g, 65.5 mmol), triethylamine (12.4 mL, 9.00 g, 89.10 mmol)

in dry dimethylformamide (300 mL) under an argon atmosphere, is treated with di-t-butyl dicarbonate (19.44 g, 89.1 mmol) and stirred at 18° C. for 18 hours. The solvent is evaporated off under reduced pressure to give a residue which is treated with aqueous citric acid solution (100 mL of 10%) and extracted with dichloromethane (2–100 mL). The combined extracts are dried ($Na_2SO_4$), filtered and the solvent is evaporated off under reduced pressure to yield the product which is purified by column chromatography on silica gel, eluent 5% methanol in dichloromethane and recrystallised from t-butylmethyl ether-hexane to give the title compound as a colourless crystalline solid.

(ii) N-(4-Methylphenyl)-2{[(1,1-dimethylethoxy) carbonyl]amino}-6-methyl]benzamide Firstly N-methylmorpholine (6.15 mL, 5.64 g, 55.8 mmol) and then O-(benzotriazol1-yl)-N,N,N',N',-tetramethyluronium hexafluorophosphate (10.15 g, 26.8 mmol) are added to a stirred mixture of 2-{[(1,1-dimethylethoxy)carbonyl]amino}-6-methylbenzoic acid (5.60 g, 22.3 mmol) and p-toluidine 4.78 g, 44.6 mmol) in dry dimethylformamide (110 mL) under an argon atmosphere, and stirred at 18° C. for 16 hours. The solvent is evaporated off under reduced pressure to give a residue which is treated with aqueous sodium hydrogen carbonate solution (200 mL of 10%) and extracted with dichloromethane (3×100 mL). The combined extracts are washed with aqueous citric acid solution (100 mL of 10%), dried ($Na_2SO_4$), filtered and the solvent is evaporated off under reduced pressure to yield the crude product which is purified by column chromatography on silica gel, eluent 20% ethyl acetate in hexane, and recrystallised from tert-butyl-methyl-ether-hexane to give the title compound as a colourless crystalline solid, m.p. 250° C.

(iii) 2-Amino-N-(4-methylphenyl)-6-methylbenzamide, hydrochloride

A stirred solution of N-(4-methylphenyl)-2-([(1,1-dimethylethoxy)carbonyl]amino]-6-methyl-benzamide (1.67 g, 4.90 mmol) in methanol (4 mL) under an argon atmosphere, is treated with a saturated solution of hydrogen chloride in dioxane (30 mL) and stirred at 180° C. for 210 minutes.

The solvent is evaporated off under reduced pressure to give the crude product which is purified by recrystallisation from methanol—di-isopropyl ether to give the title compound as a colourless crystalline solid, m.p. 217–220° C.

EXAMPLES

Example 1

2-[(4-Pyridyl)methyl]amino-N-[4-(trifluoromethyl) phenyl]benzamide

Sodium cyanoborohydride (0.80 g of 90%, 11.5 mmol) is added in portions over 30 minutes to a stirred mixture of acetic acid (0.15 mL), 4-pyridinecarboxaldehyde (1.00 g, 3.57 mmol) and intermediate 2a (1.00 g, 3.57 mmol) in methanol (15 mL) at 25° C. under an argon atmosphere. The mixture is stirred for 16 hours, diluted with dichloromethane (100 mL) and treated with a saturated aqueous solution of sodium hydrogen carbonate (50 mL). The mixture is stirred for an additional 5 min and then extracted with dichoromethane (3×50 mL). The combined extracts are dried ($Na_2SO_4$) and the solvent is evaporated off under reduced pressure to yield the crude product that is purified by column chromatography on silica gel, eluent 33% ethyl acetate in hexane, and recrystallised from 2-propanol—hexane to give the title compound as a colourless crystalline solid, m.p. 171–175° C. and having the following physical characteristics: $^1$H-NMR (DMSO-$d_6$)d 4.49 (d, J=6.1 Hz, 2H), 6.56 (d, J=8.4 Hz, 1 H), 6.6 (t, J=8.5 Hz, 1H), 7.26 (t, J=8.4 Hz, 1H), 7.33 (d, J=5.9 Hz, 2H), 7.71 (d, J=8,5 Hz, 2H), 7.72 (m, 1H), 7.90 (t, J=6.1 Hz, 1H), 7.96 (d, J=8.5 Hz, 2H), 8.49 (d, J=5.9 Hz, 2H) and 10.46 (s, 1H).

The following compounds are prepared analogously by utilising the appropriate amine:

Example 2

2-[(4-Pyridyl)methyl]amino-N-[3-fluoro-(4-trifluoromethyl)phenyl]benzamide, m.p. 162–164° C., utilising intermediate 2b Example 3

2-[(4-Pyridyl)methyl]amino-N-phenylbenzamide, m.p. 160–161° C., utilising 2-aminobenzanilide Example 4

2-[(4-Pyridyl)methyl]amino-N-(4chlorophenyl) benzamide, m.p. 134–139° C., utilising intermediate 2c Example 5

2-[(4-Pyridyl)methyl]amino-N-(4-methylphenyl) benzamide, utilising intermediate 2d Example 6

2-[(4-Pyridyl)methyl]amino-N-(3-fluoro-4-methylphenyl)benzamide is prepared utilising intermediate 2e.

Following purification by chromatography (silica gel, eluent 33% ethyl acetate in hexane), the base is dissolved in ethyl acetate and treated with a solution of hydrogen chloride in dichloromethane. The precipitated product is filtered off and recrystallized from dichloromethane-hexane to afford the dihydrochloride salt, m.p. 116–124° C.

Example 7

2-[(4-Pyridyl)methyl]amino-N-[4chloro-3-(trifluoromethyl7phenyl:benzamide, m.p. 162 –1 72° C., utilising intermediate 2f Example 8

2-[(4-Pyridyl)methyl]amino-N-[3-chloro-5-(trifluoromethyl)phenyl]benzamide, m.p. 190–194° C., utilising intermediate 2g Example 9

2-[(4-Pyridyl)methyl]amino-N-[4-fluoro-3-(trifluoromethyl)phenyl]benzamide, m.p. 183–185° C., utilising intermediate 2h Example 10

2-[(4-Pyridyl)methyl]amino-N-[3-fluoro-5-(trifluoromethyl)phenyl]benzamide, m.p. 196–197°C., utilising intermediate 2i Example 11

2-[(4-Pyridyl)methyl]amino-N-[3,5-(bistrifluoromethyl)phenyl]benzamide, m.p. 180–185° C., utilising intermediate 2j Example 12

2-[(4-Pyridyl)methyl]amino-N-[3,4-(bistrifluoromethyl)phenyl]benzamide, utilising intermediate 2k Example 13

2-[(4-Pyridyl)methyl]amino-N-[3-methoxy-5-(trifluoromethyl)phenyl]benzamide, m.p. 134–136° C., utilising intermediate 2l Example 14

2-[(4-Pyridyl)methyl]amino-N-[3-(trifluoromethyl) phenyl]benzamide, m.p. 157–159° C., utilising intermediate 2m Example 15

2-[(4-Pyridyl)methyl]amino-N-[3-(1,1-dimethylethyl)phenyl]benzamide, m.p. 144–147° C., utilising intermediate 2n

Example 16

2-[(4-Pyridyl)methyl]amino-N-(3-cyanophenyl) benzamide. m.p. 157–160° C. utilising intermediate 2o

Example 17

2-[(4-Pyridyl)methyl]amino-N-(3-methylthio) phenyl]benzamide, m.p. 138–142° C., utilising intermediate 2p

Example 18

2-[(4-Pyridyl)methyl]amino-N-(3-acetylaminophenyl)benzamide, m.p. 157–158° C., utilising intermediate 2q

Example 19

2-[(4-Pyridyl)methyl]amino-N-[3-[(aminocarbonyl) amino]phenyl]benzamide, m.p. 200–202° C., utilising intermediate 2r

Example 20

2-[(4-Pyridyl)methyl]amino-N-[3-(dimethylamino) phenyl]benzamide, m.p. 152–154° C., utilising intermediate 2s

Example 21

5-Methoxy-2-[(4-pyridyl)methyl]amino-N-[3-(trifluoromethyl)phenyl]benzamide, m.p. 175–178° C., utilising intermediate 2t

Example 22

3-Methyl-2-[(4-pyridyl)methyl]amino-N-[3-(trifluoromethyl)phenylbenzamide is prepared utilising intermediate 2u Following purification by column chromatography (silica gel, eluent 33% hexane in ethyl acetate) the base is dissolved in ethyl acetate and treated with a solution of hydrogen chloride in dichloromethane. The precipitated product is filtered off and recrystallized from ethyl acetate to afford the dihydrochloride salt, m.p. 94–98°C.

Example 23

4,5Difluoro-2-(4-pyridyl)methyl]amino-N-[3-(trifluoromethyl)phenyl]benzamide, m.p. 175–178° C., utilising intermediate 2v

Example 24

2-[(4-Pyridyl)methyl]amino-N-methyl-N-3-(trifluoromethyl)pheny]benzamide, m.p. 127–128° C., utilising intermediate 2w

Example 25

2-[(4-Pyridyl)methyl]amino-N-(3-methylsulphonyl) phenyl]benzamide, m.p. 178–184° C., utilising intermediate 2x

Example 26

2-[(4-Pyridyl)methyl]amino-N-(3-methylsulphinylphenyl]benzamide, m.p. 175–1780° C. utilising intermediate 2y

Example 27

2-[(4-Pyridyl)methyl]amino-N-[4-(1,1-dimethylethyl)phenyl]benzamide, m.p. 168–170° C., utilising intermediate 2z

Example 28

2-[(4-Pyridyl)methyl]amino-N-(3-chlorophenyl) benzamide, m.p. 131–133° C., utilising intermediate 2aa

Example 29

2-[(4-Pyridyl)methyl]amino-N-(3-bromophenyl) benzamide, m.p. 156–159° C., utilising intermediate 2ab

Example 30

2-[(4-Pyridyl)methyl]amino-N-(3-methylphenyl) benzamide, m.p. 139–140° C., utilising intermediate 2ac

Example 31

2-[(4-Pyridyl)methyl]amino-N-(3-benzoylphenyl) benzamide, m.p. 168–169° C., utilising intermediate 2ad

Example 32

2-[(4-Pyridyl)methyl]amino-N-[3-(aminocarbonyl) phenyl]benzamide, m.p. 195–203° C., utilising intermediate 2ae

Example 33

2-[(4-Pyridyl)methyl]amino-N-(4-methylphenyl)-6-methylbenzamide, m.p. 162–163° C., utilising intermediate 2at The following compounds are prepared by a method analogous to that described in Example 14, by utilising the appropriate aldehyde:

Example 34

2-[(3-Pyridyl)methyl]amino-N-[3-(trifluoromethyl) phenyl]benzamide, m.p. 140–142° C., utilising 3-pyridinecarboxaldehyde

Example 35

2-[(4-Quinolinyl)methyl]amino-N-[3-(trifluoromethyl)phenyl]benzamide, m.p. 191–193° C., utilising 4-quinolinecarboxaldehyde

Example 36

2-[(5-Quinolinyl)methyl]amino-N-[3-(trifluoromethyl)phenyl]benzamide, m.p. 176–178° C., utilising 5-quinolinecarboxaldehyde prepared as described by Wommack et al, J.Het.Chem. 1969;6: 243–245, from 5-aminoquinoline

Example 37

2-[(4-(2-Methyl)pyridyl)methyl]amino-N-[3-(trifluoromethyl)phenyl]benzamide, m.p. 146–147° C., utilising 2-methyl-4-pyridinecarboxaldehyde prepared as described by Boehm et al, J. Med. Chem. 1996;39:3929–3937 from 2-methyl-4-cyanopyridine, which was in turn prepared by the method of *Ashimori et al, Chem. Pharm. Bull.* 1990;38:2446–2458 from 2-methylpyridine-1-oxide

Example 38

2-[(4-(1,2-Dihydro-2-oxo)pyridyl)methyl]amino-N-[3-(trifluoromethyl)phenyl]benzamide, m.p. 183–185° C., utilising 1,2-dihydro-2-oxo4-pyridinecarboxaldehyde prepared as described by Ren, Sakai and Nakanishi, J. Amer. Chem. Soc. 1997;119:3619–3620 from 2-hydroxy-4-methylpyridine

Example 39

2-[(4-Quinolinyl)methyl]amino-N-(4-chlorophenyl) benzamide, m.p. 178–209° C., is prepared by a method analogous to that described in Example 4, by utilising 4quinolinecarboxaldehyde

Example 40

2-[(2-Imidazolyl)methyl]amino-N-(4-chlorophenyl) benzamide, m.p. 181–184° C., is prepared by a method analogous to that described in Example 4, by utilising 1H-imidazole-2-carboxaldehyde

Example 41

2-[2-(4-Pyridyl)ethyl]amino-N-[3-(trifluoromethyl) phenyl]benzamide

4-Pyridineethanamine (Maybridge Chemical Co, Cornwall, England; 0.31 g , 2.5 mmol) is added to a stirred mixture of 2-bromo-N-[3-(trifluoromethyl)phenyl] benzamide (intermediate 1x; 1.72 g, 5 mmol), powdered potassium carbonate (0.35 g, 2.5 mmol) and copper(1)iodide (Fluka, Buchs, Switzerland; 0.48 g, 2.5 mmol) in dimethylformamide (10 mL). The resulting mixture is then purged with argon and subsequently heated at 160° C. under an argon atmosphere for 15 hours. The mixture is cooled, treated with water (100 mL) and extracted with ethyl acetate (3×80 mL). The combined extracts are washedwith an aqueous solution of ammonia (2–10%), dried (Na$_2$SO$_4$), filtered and the solvent is evaporated off under reduced pressure to yield the crude product which is purified by column chromatography on silica gel, eluent 50% ethyl acetate in hexane and recrystallised from ethyl acetate-hexane to give the title compound as a colourless crystalline solid, m.p. 151–152° C.

The following compounds are prepared by a method analogous to that described in Example 41, by utilising the appropriate amine:

Example 42

2-[2-(3-Pyridyl)ethyl]amino-N-[3-(trifluoromethyl) phenyl]benzamide, m.p. 102–103° C., utilising 3-pyridineethanamine (Maybridge Chemical Co, Cornwall, England).

Example 43

2-[1-Methyl-2-(3-pyridyl)ethyl]amino-N-[3-(trifluoromethyl)phenyl]benzamide, utilising 1-(3-pyridyl)-2-propylamine prepared as described by in J. Amer. Chem. Soc. 1997;119:3619–3620

Example 44

2-[(1-Oxido-4-pyridyl)methyl]amino-N-[3-(trifluoromethyl)phenyl]benzamide

3-Chloroperoxybenzoic acid (2.06 g of 70%, 8.4 mmol) is added to a stirred mixture of 2-[(4-pyridyl)methyl]amino-N-[3-(trifluoromethyl)phenyl]benzamide (Example 14; 1.86 g, 5 mmol) in dichloromethane (50 mL) at 0° C. The resulting mixture is then stirred at room temperature for 15 hours. The mixture is diluted with dichloromethane (100 mL) and washed sequentially with aqueous sodium hydroxide (2×100 mL) and aqueous sodium thiosulphate (2×50 mL of 10%). The organic phase is dried (Na$_2$SO$_4$), filtered and the solvent is evaporated off under reduced pressure to yield the crude product which is purified by column chromatography on silica gel, eluent 20% ethanol in ethyl acetate, and recrystallised from ethyl acetate-hexane to give the title compound as a colourless crystalline solid, m.p. 181–184° C.

Example 45

2-[(4-Pyridyl)methyl]methylamino-N-[3-(trifluoromethyl)phenyl]benzamide

Sodium cyanoborohydride (0.55 g, 14.1 mmol) is added to a stirred mixture of paraformaldehyde (0.82 g, 27.3 mmol) and 2-[(4-pyridyl)methyl]amino-N-[3-(trifluoromethyl)phenyl]benzamide (Example 14; 1.03 g, 2.78 mmol) in tetrahydrofuran (30 mL) at 20° C. under an argon atmosphere. The resulting mixture is then treated dropwise with trifluoroacetic acid (15 mL) and stirred at room temperature for 20 hours. The mixture diluted with ice-cold aqueous sodium hydroxide (100 mL of 5M) and extracted with dichloromethane (3×100 mL). The organic phase is dried (Na$_2$SO$_4$), filtered and the solvent is evaporated off under reduced pressure to yield the crude product which is purified by column chromatography on silica gel, eluent ethyl acetate, to give the title compound as a colourless crystalline solid.

Example 46

2-[(4-Pyridyl)methyl]methylamino-N-(4-chloronaphthyl)benzamide 0.75 ml Trimethylaluminium (2M in toluene) is added to a suspension of 266 mg 4-chloro-1-naphthylamine in 1 mL toluene. After 10 minutes a cold solution of 242 mg methyl N-(4-pyridylmethyl)-anthranilate in 2 mL toluene is added. The mixture is stirred for 1 hour at room temperature and for 1 hour under reflux. After cooling to room temperature saturated NaHCO$_3$ solution is added and the mixture extracted with ethyl acetate. The extract is washed with water and saturated sodium chloride solution and concentrated. The residue is crystallized with ethyl acetate to. give the title compound as a solid with m.p. 137° C.

Stage 46.1: N-(4-pyridylmethyl)-anthranilate 3 mL Acetic acid and 8.6 g 4-pyridinecarbaldehyde are added to a solution of 7.5 g methyl anthranilate in 300 mL methanol. The mixture is stirred for 12 hours under nitrogen atmosphere at room temperature. 5.7 g Sodium cyanotrihydridoborate (85%) is added and the mixture is stirred for 3 hours at room temperature. Additional 1.14 g sodium cyanotrihydridoborate (85%) is added and the mixture is stirred for 12 hours at room temperature. The solvent is evaporated and the residue dissolved in ethyl acetate and washed with saturated NaHCO$_3$ solution and saturated sodium chloride solution. The organic extract is concentrated and purified with hexane/ethyl acetate (1:1) on silica gel to yield methyl N-(4-pyridylmethyl)-anthranilate with m.p. 86° C.

Examples 47–72

The compounds of Examples 47–72 were prepared in an analogous manner by reductive amination followed by amidation with an amine and trimethylaluminium as described in Example 46. The used anthranilic esters are commercially available or are described below.

Synthesis of the Starting Material for Example 47

2-Methyl-6-nitrobenzoic acid is reacted with trimethylsilyldiazomethane to yield methyl 2-methyl-6-nitrobenzoate with m.p. 44–45° (Chem. Pharm. Bull., Vol. 29, 1475 (1981)). Methyl 2-methyl-6-nitrobenzoate is hydrogenated in methanol in the presence of palladium, 10% on carbon powder, at room temperature and atmospheric pressure to give methyl 2-methyl-6-aminobenzoate.

Synthesis of the Starting Material for Example 48

2-Amino-6-chlorobenzoic acid is reacted with trimethylsilyldiazomethane to yield methyl 2-amino-6-chlorobenzoate (Chem. Pharm. Bull. Vol. 29, 1475 (1981)).

Synthesis of the Starting Material for Example 49

3,4-Methylenedioxy-6-nitrobenzaldehyde is converted to methyl 3,4-methylenedioxy-1-nitrobenzoate in methanol in the presence of sodium cyanide and manganese dioxide Synthetic Commun., 27(7), 1281–1283 (1997)). Methyl 3,4-methylenedioxy-6-nitrobenzoate is hydrogenated in ethanol in the presence of palladium, 10% on carbon powder, at room temperature and atmospheric pressure to give methyl 3,4-methylenedioxy-6-aminobenzaote.

Synthesis of the Starting Material for Example 50

0.14 g Sodium nitrite in water is added to 1 g 4,5-dimethyl-2-nitroaniline in 3 mL conc. HCl and stirred for 1 hour at +4° C. This solution is added to a mixture of 0.67 g copper (I) cyanide, 0.98 g sodium cyanide, 0.32 g sodium carbonate, 25 mL of water and 3 mL toluene. The mixture is stirred for 12 hours at room temperature and worked up to give 0.45 g 4,5-dimethyl-2-nitrobenzonitrile. 4,5-Dimethyl-2-nitrobenzonitrile is reduced with iron power in acetic acid to yield 4,5-dimethyl-2-aminobenzonitrile. 4,5-Dimethyl-2-aminobenzonitrile is heated at reflux for 12 hours in conc. HCl to give 4,5-dimethyl-2-aminobenzoic acid. 4,5-Dimethyl-2-aminobenzoic acid is reacted with trimethylsilyldiazomethane to yield methyl 4,5-dimethyl-2-aminobenzoate (Chem. Pharm. Bull. Vol. 29, (1981)).

TABLE 1

Examples 47–72
The following compounds are compounds of formula I wherein W is O, X is NH, Y is CH$_2$, R$_2$ is 4-pyridyl; R$_6$ and R$_7$ are H.

| Ex. | R$_1$ | R$_3$ | R$_4$ | R$_5$ | mp. |
|---|---|---|---|---|---|
| 47 | 4-chlorophenyl | methyl | H | H | 190 |
| 48 | 4-chlorophenyl | chloro | H | H | 183–185 |
| 49 | 4-chlorophenyl | H | -O-CH$_2$-O- | | |
| 50 | 4-chlorophenyl | H | methyl | methyl | |
| 51 | 4-n-propylphenyl | H | chloro | H | |
| 52 | 4-n-propylphenyl | H | H | H | |
| 53 | 7-hydroxynaphthyl | H | H | H | |
| 54 | 8-hydroxy-2-naphthyl | H | H | H | 235 |
| 55 | 4-chlorophenyl | H | H | chloro | 186 |
| 56 | 4-chlorophenyl | H | methyl | H | 127 |
| 57 | 5,6,7,8-tetrahydro-naphthyl | H | H | H | 116 |
| 58 | 4-biphenyl | H | H | H | 135–136 |
| 59 | 4-chlorophenyl | H | chloro | H | 206–207 |
| 60 | naphthyl | H | H | H | |
| 61 | 2-napthyl | H | H | H | 159–160 |
| 62 | 4-methoxyphenyl | H | H | H | |
| 63 | 3-trifluoromethoxy-phenyl | H | H | H | |
| 64 | 4-methoxy-2-naphthyl | H | H | H | 152–154 |
| 65 | 3-bromo-2-naphthyl | H | H | H | 131–132 |
| 66 | 4-(isopropoxy-carbonyl)-phenyl | H | H | H | 70 |
| 67 | 4-trifluoromethoxy-phenyl | H | H | H | |
| 68 | 4-(isopropyl-carbamoyl)-phenyl | H | H | H | 79 |
| 69 | 3-chloro-4-methylphenyl | H | H | H | 143 |
| 70 | 2-methylphenyl | H | H | H | 143 |
| 71 | 3-(methoxy-carbonylmethyl)-phenyl | H | H | H | |
| 72 | 4-phenoxyphenyl | H | H | H | |

Example 73
Test for Activity Flt-1 VEGF-Receptor Tyrosine Kinase

The test is conducted using Flt-1 VEGF-receptor tyrosine kinase, as described hereinabove. The IC$_{50}$ are given below, insofar as they have been accurately recorded:

TABLE 2

Test for activity against Flt-1 VEGF-receptor tyrosine kinase

| Title compound from Example | IC$_{50}$ ($\mu$M) |
|---|---|
| 4 | 0.18 |
| 5 | 0.26 |
| 7 | 0.56 |

Example 74
Soft Capsules 5000 soft gelatin capsules, each comprising as active ingredient 0.05 g of one of the compounds of formula I mentioned in the preceding Examples, are prepared as follows:

| Composition | |
|---|---|
| Active ingredient | 250 g |
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

What is claimed is:

1. A method of treating a warm-blooded animal with a neoplastic disease that responds to an inhibitor of VEGF receptor tyrosine kinase, which comprises administering to the warm-blooded animal an effective amount of a compound of formula I,

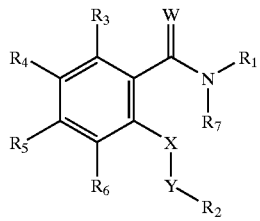

(I)

wherein

W is O or S

X is $NR_8$;

Y is $CR_9R_{10}$—$(CH_2)_n$ wherein $R_9$ and $R_{10}$ are independently of each other hydrogen or lower alkyl, and n is an integer of from and including 0 to and including 3; or Y is $SO_2$;

$R_1$ is aryl;

$R_2$ is a 5- or 6-member heteroaryl ring comprising one ring nitrogen;

any of $R_3$, $R_4$, $R_5$ and $R_6$, independently of the other, is H, halogen, lower alkyl or two adjacent substituents together are lower alkylene dioxy; and $R_7$ and $R_8$, independently of each other, are H or lower alkyl;

or an N-oxide or a pharmaceutically acceptable salt thereof.

2. A compound of formula I,

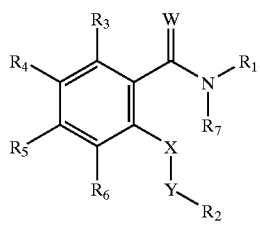

(I)

wherein

W is O or S;

X is $NR_8$;

Y is $CR_9R_{10}$—$(CH_2)_n$ wherein $R_9$ and $R_{10}$ are independently of each other hydrogen or lower alkyl, and n is an integer of from and including 0 to and including 3; or Y is $SO_2$;

$R_1$ is aryl;

$R_2$ is a 5- or 6-member heteroaryl ring comprising one ring nitrogen;

any of $R_3$, $R_4$, $R_5$ and $R_6$ independently of the other, is H, halogen, lower alkyl or two adjacent substituents together are lower alkylene dioxy; and $R_7$ and $R_8$, independently of each other, are H or lower alkyl;

with the exception of the compound of formula I wherein W is O, X is $NR_6$, Y is $CH_2$, $R_1$ is 4-chlorophenyl, $R_2$ is 2-pyridyl, $R_3$, $R_4$, $R_5$, $R_7$ and $R_8$ are each H and $R_6$ is chloro;

or a N-oxide or a pharmaceutically acceptable salt thereof.

3. A compound of formula I according to claim 2, wherein

W is O;

X is $NR_8$;

Y is $CH_2$;

$R_1$ is phenyl, naphthyl or 5,6,7,8-tetrahydronaphthyl which is in each case either unsubstituted or independently substituted by one or two substituents selected from the group comprising halogen; lower alkyl; lower alkoxy; hydroxy; phenyl; phenoxy; halogen-lower alkoxy; lower alkoxycarbonyl; N-lower alkyl carbamoyl; and lower alkoxycarbonyl lower alkyl;

$R_2$ is 4-pyridyl;

any of $R_3$, $R_4$, $R_5$ and $R_6$, independently of the other, are H, methyl or chloro; or $R_3$ and $R_4$ together represent methylene dioxy and $R_5$ and $R_6$, independently of the other, are H, methyl or chloro; and $R_7$ and $R_8$ are H;

or a N-oxide or a pharmaceutically acceptable salt thereof.

4. A compound of formula I according to claim 2 selected from

2-[(4-pyridyl)methyl]amino-N-(4-trifluoromethylphenyl)benzamide;
2-[(4-pyridyl)methyl]amino-N-(4-chlorophenyl)benzamide;
2-[(4-pyridyl)methyl]amino-N-(4-methylphenyl)benzamide;
2-[(4-pyridyl)methyl]amino-N-(3-fluoro-4-methylphenyl)benzamide;
2-[(4-pyridyl)methyl]amino-N-(4-chloro-3-trifluoromethylphenyl)benzamide;
2-[(4-pyridyl)methyl]amino-N-(3-chloro-5-trifluoromethylphenyl)benzamide; and
2-[(4-pyridyl)methyl]amino-N-(4-methylphenyl)-6-methylbenzamide;

or a pharmaceutically acceptable salt thereof.

5. A compound of formula I according to claim 2 selected from

2-[(4-pyridyl)methyl]amino-N-[3-fluoro-(4-trifluoromethyl)phenyl]benzamide;
2-[(4-pyridyl)methyl]amino-N-phenylbenzamide;
2-[(4-pyridyl)methyl]amino-N-[4-fluoro-3-(trifluoromethyl)phenyl]benzamide;
2-[(4-pyridyl)methyl]amino-N-[3-fluoro-5-(trifluoromethyl)phenyl]benzamide;

2-[(4-pyridyl)methyl]amino-N-[3,5-(bistrifluoromethyl)phenyl]benzamide;
2-[(4-pyridyl)methyl]amino-N-[3,4-bis-(trifluoromethyl)phenyl]benzamide;
2-[(4-pyridyl)methyl]amino-N-[3-methoxy-5-(trifluoromethyl)phenyl]benzamide;
2-[(4-pyridyl)methyl]amino-N-[3-(trifluoromethyl)phenyl]benzamide;
2-[(4-pyridyl)methyl]amino-N-[3-(1,1-dimethylethyl)phenyl]benzamide;
2-[(4-pyridyl)methyl]amino-N-(3-cyanophenyl)benzamide;
2-[(4-pyridyl)methyl]amino-N-[3-methylthio)phenyl]benzamide;
2-[(4-pyridyl)methyl]amino-N-(3-acetylaminophenyl)benzamide;
2-[(4-pyridyl)methyl]amino-N-[3-[(aminocarbonyl)amino]phenyl]benzamide;
2-[(4-pyridyl)methyl]amino-N-[3-(dimethylamino)phenyl]benzamide;
5-methoxy-2-[(4-pyridyl)methyl]amino-N-[3-(trifluoromethyl)phenyl]benzamide;
3-methyl-2-[(4-pyridyl)methyl]amino-N-[3-(trifluoromethyl)phenyl]benzamide;
4,5-difluoro-2-[(4-pyridyl)methyl]amino-N-[3-trifluoromethyl)phenyl]benzamide;
2-[(4-pyridyl)methyl]amino-N-[3-(trifluoromethyl)phenyl]benzamide;
2-[(4-pyridyl)methyl]amino-N'-methyl-N'-[3-(trifluoromethyl)phenyl]benzamide;
2-[(4-pyridyl)methyl]amino-N-[(3-methylsulphonyl)phenyl]benzamide;
2-[(4-pyridyl)methyl]amino-N-[(3-methylsulphinylphenyl]benzamide;
2-[(4-pyridyl)methyl]amino-N-[4-(1,1-dimethylethyl)phenyl]benzamide;
2-[(4-pyridyl)methyl]amino-N-(3-chlorophenyl)benzamide;
2-[(4-pyridyl)methyl]amino-N-(3-bromophenyl)benzamide;
2-[(4-pyridyl)methyl]amino-N-(3-methylphenyl)benzamide;
2-[(4-pyridyl)methyl]amino-N-(3-benzoylphenyl)benzamide;
2-[(4-pyridyl)methyl]amino-N-[3-(aminocarbonyl)phenyl]benzamide;
2-[(3-pyridyl)methyl]amino-N-[3-(trifluoromethyl)phenyl]benzamide;
2-[(4-(2-methyl)pyridyl)methyl]amino-N-[3-(trifluoromethyl)phenyl]benzamide;
2-[2-(4-pyridyl)ethyl]amino-N-[3-(trifluoromethyl)phenyl]benzamide;
2-[2-(3-pyridyl)ethyl]amino-N-[3-(trifluoromethyl)phenyl]benzamide;
2-[1methyl-2-(3-pyridyl)ethyl]amino-N-[3-(trifluoromethyl)phenyl]benzamide;
2-[(1-oxido-4-pyridyl)methyl]amino-N-[3-(trifluoromethyl)phenyl]benzamide; and
2-[(4-pyridyl)methyl]methylamino-N-[3-(trifluoromethyl)phenyl]benzamide;

or a pharmaceutically acceptable salt thereof.

6. A compound of formula I according to claim 2 selected from

2-[(4-pyridyl)methyl]amino-N-(4-chloronaphthyl)benzamide;
6-methyl-2-[(4-pyridyl)methyl]amino-N-(4-chlorophenyl)benzamide;
6-chloro-2-[(4-pyridyl)methyl]amino-N-(4-chlorophenyl)benzamide;
3,4-methylendioxy-6-[(4-pyridyl)methyl]amino-N-(4-chlorophenyl)benzamide;
4,5-dimethyl-2-[(4-pyridyl)methyl]amino-N-(4-chlorophenyl)benzamide;
5-chloro-2-[(4-pyridyl)methyl]amino-N-(4-n-propylphenyl)benzamide;
2-[(4-pyridyl)methyl]amino-N-(4-n-propylphenyl)benzamide;
2-[(4-pyridyl)methyl]amino-N-(7-hydroxynaphthyl)benzamide;
2-[(4-pyridyl)methyl]amino-N-(8-hydroxy-2-naphthyl)benzamide;
4-chloro-2-[(4-pyridyl)methyl]amino-N-(4-chlorophenyl)benzamide;
5-methyl-2-[(4-pyridyl)methyl]amino-N-(4-chlorophenyl)benzamide;
2-[(4-pyridyl)methyl]amino-N-(5,6,7,8-tetrahydronaphthyl)benzamide;
2-[(4-pyridyl)methyl]amino-N-(4-biphenyl)benzamide;
5-chloro-2-[(4-pyridyl)methyl]amino-N-(4chlorophenyl)benzamide;
2-[(4-pyridyl)methyl]amino-N-(naphthyl)benzamide;
2-[(4-pyridyl)methyl]amino-N-(2-napthyl)benzamide;
2-[(4-pyridyl)methyl]amino-N-(4-methoxyphenyl)benzamide;
2-[(4-pyridyl)methyl]amino-N-[3-(trifluoromethoxy)phenyl]benzamide;
2-[(4-pyridyl)methyl]amino-N-(4-methoxy-2-naphthyl)benzamide;
2-[(4-pyridyl)methyl]amino-N-(3-bromo-2-naphthyl)benzamide;
2-[(4-pyridyl)methyl]amino-N-[4-(isopropoxycarbonyl)phenyl]benzamide;
2-[(4-pyridyl)methyl]amino-N-[4-(trifluoromethoxy)phenyl]benzamide;
2-[(4-pyridyl)methyl]amino-N-[4-(isopropylcarbamoyl)phenyl]benzamide;
2-[(4-pyridyl)methyl]amino-N-(3-chloro-4-methylphenyl)benzamide;
2-[(4-pyridyl)methyl]amino-N-(2-methylphenyl)benzamide;
2-[(4-pyridyl)methyl]amino-N-[3-(methoxycarbonylmethyl)phenyl]benzamide; and
2-[(4-pyridyl)methyl]amino-N-(4-phenoxyphenyl)benzamide;

or a pharmaceutically acceptable salt thereof.

7. A pharmaceutical preparation, comprising a compound of formula I according to claim 2 or a N-oxide or a pharmaceutically acceptable salt thereof, or a hydrate or solvate thereof, and at least one pharmaceutically acceptable carrier.

8. A process for the preparation of a compound of formula I according to claim 2 or a N-oxide or a pharmaceutically acceptable salt thereof, characterized in that a) for the synthesis of a compound of the formula I wherein X represents $NR_8$, where $R_8$ is hydrogen and Y represents $CHR_9-(CH_2)_n$, each as indicated for a compound of formula I and the remaining symbols W, $R_1$, $R_2$, $R_3$, $R_4$, $R_5$, $R_6$ and $R_7$ are as defined for a compound of the formula I an aniline derivative of the formula II

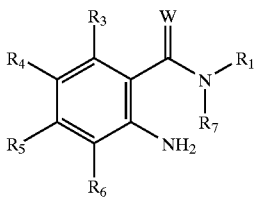

(II)

wherein W, $R_1$, $R_3$, $R_4$, $R_5$, $R_6$ and $R_7$ are as defined for a compound of the formula I is reacted with a carbonyl compound of the formula III $$R_2\text{—}(CH_2)_n\text{—}C(R_9)\text{=}O \quad \text{(III)}$$

wherein n, $R_2$ and $R_9$ are as defined for a compound of the formula I in the presence of a reducing agent or b) for the synthesis of a compound of the formula I wherein X is SO2 and the remaining symbols $R_1$, $R_2$, $R_3$, $R_4$, $R_5$, $R_6$, $R_7$, W and X are as defined for a compound of the formula I an aniline derivative of the formula II as defined under process variante a) is reacted with an acid of the formula IVa $$R_2\text{—}Y\text{—}OH \quad \text{(IVa)}$$

or a reactive derivative thereof; or with a compound of formula IVb, $$R_2\text{—}Y\text{—}Hal' \quad \text{(IVb)}$$

wherein Hal' is chloro, bromo or iodo; or c) for the synthesis of compounds of the formula I wherein X represents $NR_8$, Y represents $CR_9R_{10}$—$(CH_2)_n$ and the remaining symbols $R_1$, $R_2$, $R_3$, $R_4$, $R_5$, $R_6$, $R_7$ and $R_8$ are as defined for a compound of the formula I a halogen derivative of the formula V

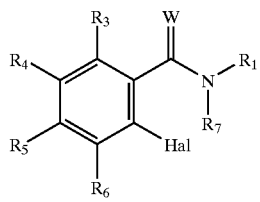

(V)

wherein Hal represents iodine, bromine or chlorine and W, $R_1$, $R_3$, $R_4$, $R_5$, $R_6$ and $R_7$ are as defined for a compound of the formula I is reacted with am amine of the formula VI $$R_2\text{—}(CH_2)_n\text{—}C(R_9)(R_{10})\text{—}NHR_8 \quad \text{(VI)}$$

wherein n, $R_2$, $R_8$, $R_9$ and $R_{10}$ are as defined for a compound of the formula I in the presence of an appropriate catalyst in an inert solvent in the presence of an aprotic base;

where the starting compounds defined in a), b) or c) may also be present with functional groups in protected form if necessary and/or in the form of salts, provided a salt-forming group is present and the reaction in salt form is possible;

any protecting groups in a protected derivative of a compound of the formula I are removed; and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

9. A method of treating a warm-blooded animal with retinopathy or age-related macular degeneration, which comprises administering to the warm-blooded animal an effective amount of a compound of formula I,

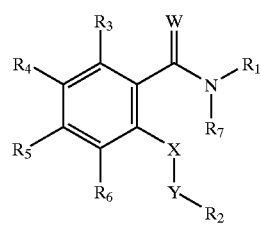

(I)

wherein
  W is O or S;
  X is $NR_8$;
  Y is $CR_9R_{10}$—$(CH_2)_n$ wherein
    $R_9$ and $R_{10}$ are independently of each other hydrogen or lower alkyl, and n is an integer of from and including 0 to and including 3; or
  Y is $SO_2$;
  $R_1$ is aryl;
  $R_2$ is a 5- or 6-member heteroaryl ring comprising one ring nitrogen;
  any of $R_3$, $R_4$, $R_5$ and $R_6$, independently of the other, is H, halogen, lower alkyl or two adjacent substituents together are lower alkylene dioxy; and
  $R_7$ and $R_8$, independently of each other, are H or lower alkyl;
or an N-oxide or a pharmaceutically acceptable salt thereof.

10. A compound of claim 2 which is not an N-oxide.

11. A compound of claim 2 wherein
  $R_1$ is phenyl that is unsubstituted or substituted by up to three substituents selected from amino, mono- or di-substituted amino wherein the substituents are selected independently from lower alkyl, hydroxy-lower alkyl, phenyl-lower alkyl, lower alkanoyl, benzoyl and substituted benzoyl wherein the phenyl radical is substituted by one or two substituents selected from nitro, amino, halogen, N-lower alkylamino, N,N-di-lower alkylamino, hydroxy, cyano, carboxy, lower-alkoxycarbonyl, lower alkanoyl and carbamoyl, and phenyl-lower alkoxycarbonyl wherein the phenyl radical is substituted by one or two substituents selected from nitro, amino, halogen, N-lower alkylamino, N,N-di-lower alkylamino, hydroxy, cyano, carboxy,lower-alkoxycarbonyl,lower alkanoyl and carbamoyl; lower alkyl; substituted lower alkyl where up to three substituents are present independently selected from the group consisting of halogen, N-lower alkylamino, N,N-di-lower alkylamino, N-lower alkanoylamino, hydroxy, cyano, carboxy, lower alkoxycarbonyl and phenyl-lower alkoxycarbonyl; hydroxy, lower alkoxy; phenyl-lower alkoxy; phenyloxy; halogen-lower alkoxy, lower alkanoyloxy; benzoyloxy; lower alkoxycarbonyloxy; phenyl-lower alkoxycarbonyloxy; nitro; cyano;carboxy; lower alkoxycarbonyl; phenyl-lower alkoxycarbonyl; phenyloxycarbonyl; lower alkylcarbonyl; carbamoyl; N-mono- or N,N-disubstituted carbamoyl that is substituted by one or two substituents independently selected from lower alkyl, phenyl-lower alkyl and hydroxy-lower alkyl at the terminal nitrogen atom; amidino; guanidino; mercapto; sulfo; lower alkylthio; phenylthio; phenyl-lower alkylthio; lower alkylphenylthio; lower alkylsulfinyl; phenylsulfinyl; phenyl-lower alkylsulfinyl; lower alkylphenylsulfinyl; lower alkanesulfonyl; phenylsulfonyl; phenyl-lower alkylsulfonyl; lower alkylphenylsulfonyl; lower alkenyl; lower alkanoyl; halogen-lower alkylmercapto; halogen-lower alkylsulfonyl; —B(OH)$_2$; and lower alkylene dioxy bound at adjacent C-atoms of the ring.

12. A compound of claim 2 wherein $R_9$ is H or methyl and n is 0.

13. A compound of claim 12 wherein
$R_1$ is phenyl, naphthyl or 5,6,7,8-tetrahydronaphthyl which is in each case either unsubstituted or independently substituted by one or two substituents selected from the group consisting of halogen; lower alkyl; lower alkoxy; hydroxy; phenyl; phenoxy; halogen-lower alkoxy; halogen-lower alkyl; lower alkoxycarbonyl; N-lower alkyl carbamoyl; lower alkylsulfinyl; lower alkanesulfonyl; and lower alkoxycarbonyl-lower alkyl.

14. A compound of claim 2 wherein $R_2$ is 2-methylpyridin-4-yl, 3-pyridyl or 4-pyridyl.

15. A compound of claim 13 wherein $R_2$ is 2-methylpyridin-4-yl, 3-pyridyl or 4-pyridyl.

16. A compound of claim 15 wherein W is O and $R_1$ is phenyl which is either unsubstituted or independently substituted by one or two substituents selected from the group consisting of halogen; lower alkyl; halogen-lower alkyl; lower alkylsulfinyl; and lower alkanesulfonyl.

17. A compound of claim 16 wherein $R_3$, $R_4$, $R_5$ and $R_6$ are independently H or methyl.

18. A compound of claim 17 wherein $R_7$ and $R_8$ are independently H, F or methyl.

19. A compound of claim 18 wherein $R_7$ and $R_8$ are independently H or methyl.

* * * * *

UNITED STATES PATENT AND TRADEMARK OFFICE
CERTIFICATE OF CORRECTION

PATENT NO. : 6,448,277 B2
DATED : September 10, 2002
INVENTOR(S) : Altmann et al.

It is certified that error appears in the above-identified patent and that said Letters Patent is hereby corrected as shown below:

Column 45,
Lines 25 and 26, delete in its entirity.

Signed and Sealed this

Fifth Day of October, 2004

JON W. DUDAS
*Director of the United States Patent and Trademark Office*